(12) United States Patent
Zaleski

(10) Patent No.: US 11,031,129 B2
(45) Date of Patent: Jun. 8, 2021

(54) SYSTEMS, METHODS, USER INTERFACES AND ANALYSIS TOOLS FOR SUPPORTING USER-DEFINABLE RULES AND SMART RULES AND SMART ALERTS NOTIFICATION ENGINE

(71) Applicant: Bernoulli Enterprise, Inc., Milford, CT (US)

(72) Inventor: John Zaleski, Elkton, MD (US)

(73) Assignee: Bernoulli Enterprise, Inc., Milford, CT (US)

( * ) Notice: Subject to any disclaimer, the term of this patent is extended or adjusted under 35 U.S.C. 154(b) by 0 days.

(21) Appl. No.: 16/599,596

(22) Filed: Oct. 11, 2019

(65) Prior Publication Data

US 2020/0185092 A1  Jun. 11, 2020

Related U.S. Application Data

(63) Continuation of application No. 15/485,522, filed on Apr. 12, 2017, now abandoned, which is a continuation of application No. 14/185,583, filed on Feb. 20, 2014, now Pat. No. 9,626,479.

(60) Provisional application No. 61/932,130, filed on Jan. 27, 2014.

(51) Int. Cl.
| | |
|---|---|
| *G06F 15/177* | (2006.01) |
| *G16H 40/63* | (2018.01) |
| *G06F 3/0482* | (2013.01) |
| *H04L 12/18* | (2006.01) |
| *G06F 16/9535* | (2019.01) |
| *G06F 19/00* | (2018.01) |
| *G16H 10/60* | (2018.01) |
| *G06F 3/0484* | (2013.01) |

(52) U.S. Cl.
CPC .......... *G16H 40/63* (2018.01); *G06F 3/0482* (2013.01); *G06F 3/04847* (2013.01); *G06F 16/9535* (2019.01); *G06F 19/00* (2013.01); *G16H 10/60* (2018.01); *H04L 12/1813* (2013.01)

(58) Field of Classification Search
CPC .... G16H 40/63; G16H 10/60; G06F 16/9535; G06F 3/0482; G06F 3/0847; G06F 19/00; H04L 12/1813
USPC ........................................................ 715/736
See application file for complete search history.

(56) References Cited

U.S. PATENT DOCUMENTS

| | | |
|---|---|---|
| 6,151,581 A | 11/2000 | Kraftson |
| 8,734,428 B2 | 5/2014 | Blomquist |

(Continued)

OTHER PUBLICATIONS

Medgadget.com, Alert Watch Anesthesia Info System for Actionable Display of Patient Data, 4 pages, Feb. 14, 2014.

*Primary Examiner* — Anil N Kumar
(74) *Attorney, Agent, or Firm* — K&L Gates LLP

(57) ABSTRACT

Computer implemented methods and systems operating on real-time data derived from a plurality of data sources for supporting user-definable rules and providing user notifications for providing user notifications and smart alarms. A user-interface configured to dynamically display a parameter and toggle between a tabular display and a graphical display is generated. At least one of a user-defined rule or a threshold value associated with the parameter from a user-interface element is received. A notification is provided to a user when the parameter satisfies the user-defined rule or exceeds the threshold value.

18 Claims, 23 Drawing Sheets

(56) References Cited

U.S. PATENT DOCUMENTS

| | | | |
|---|---|---|---|
| 2008/0281168 A1* | 11/2008 | Gibson | A61B 5/0205 600/301 |
| 2009/0216556 A1 | 8/2009 | Martin | |
| 2010/0057646 A1 | 3/2010 | Martin | |
| 2011/0119075 A1* | 5/2011 | Dhoble | G06Q 50/22 705/2 |
| 2014/0180711 A1* | 6/2014 | Kamen | G06Q 10/06 705/2 |

* cited by examiner

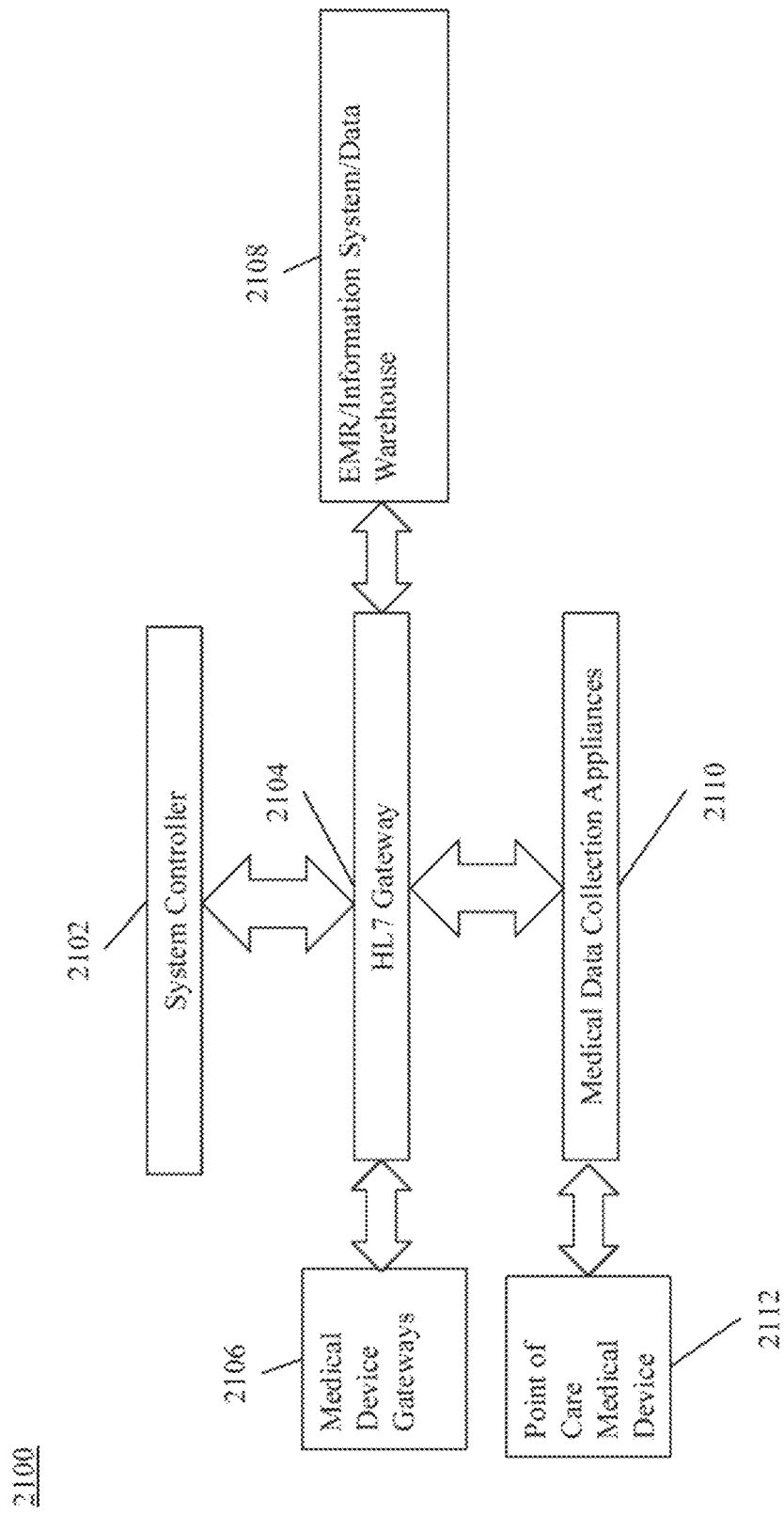

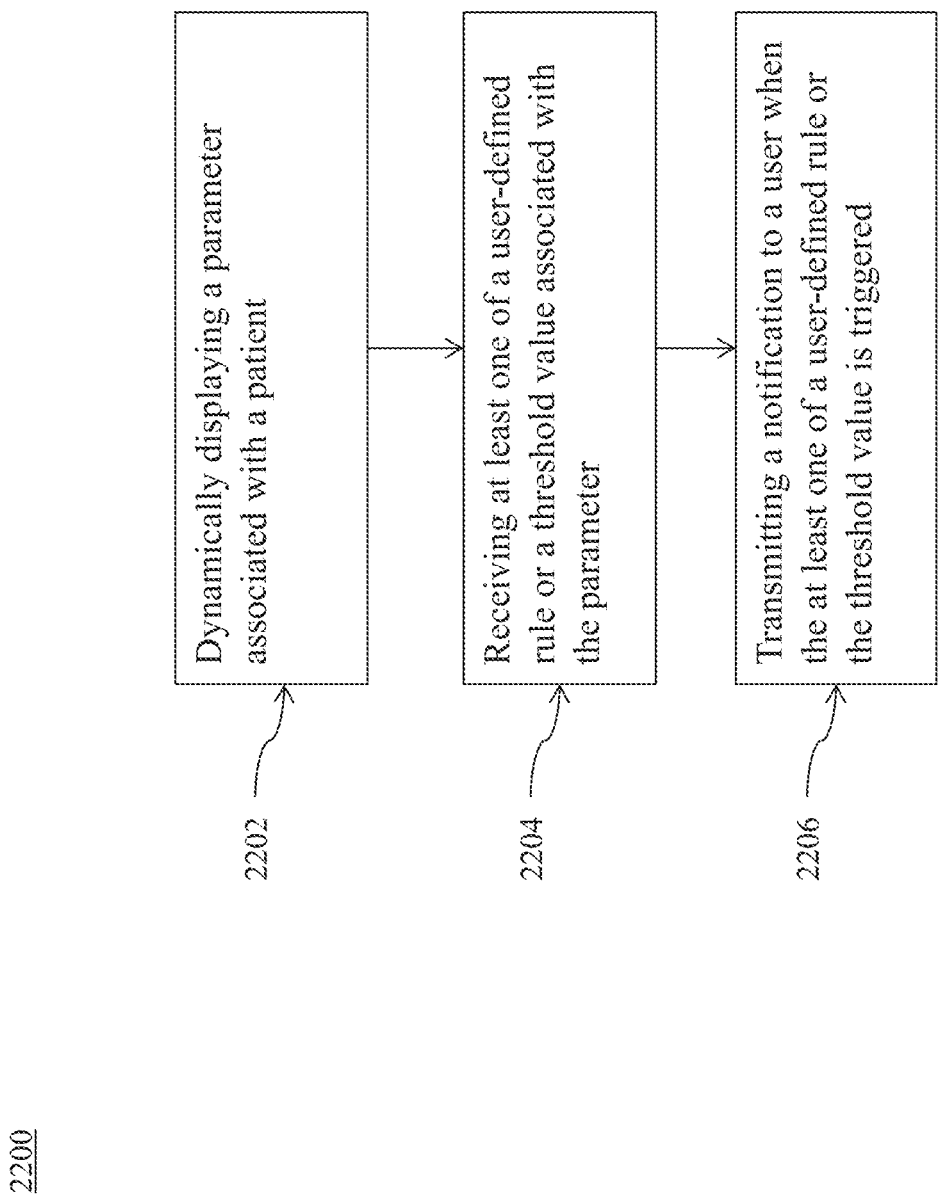

SYSTEMS, METHODS, USER INTERFACES AND ANALYSIS TOOLS FOR SUPPORTING USER-DEFINABLE RULES AND SMART RULES AND SMART ALERTS NOTIFICATION ENGINE

CROSS-REFERENCE TO RELATED APPLICATIONS

This application is a continuation of U.S. patent application Ser. No. 15/485,522 filed on Apr. 12, 2017, which is a continuation of U.S. patent application Ser. No. 14/185,583, filed on Feb. 20, 2014, which claims priority to and the benefit of U.S. Provisional Patent Application No. 61/932,130, filed on Jan. 27, 2014, the entire disclosures of each of which are incorporated by reference herein.

BACKGROUND

Many documentation systems in acute care settings of healthcare enterprises employ a user interface for documenting clinical information such as patient vital signs, infusions, outputs such as blood and urine flow, laboratory values, notes, images, and orders. The formats of many of these documentation systems are tabular and rather static in that they: (1) do not permit dynamic manipulation of formatting, or re-balancing of the view of the data in real-time; (2) are limited in that they present a singular view for all clinicians regardless of preferences; (3) are not designed to present data in real-time (i.e., down to sub-minute level of data recording); (4) do not have analysis tools to facilitate clinical trials or research or trending analysis at the point of care; (5) do not provide an easy and simple way to toggle between tabular data and graphical presentations; and (6) do not provide the capability to alter or manipulate time scale; (7) do not provide the capability to apply mathematical and statistical rules to multi-source data (e.g., data derived from multiple sources within the healthcare setting, such as vital signs, laboratory, infusions, imaging, etc.) available through these interfaces; (8) do not provide the capability for an end-user to manipulate and trial analysis tools and save preferences associated with these analysis tools; (9) provide the capability to download data for offline analysis through the user-interface; or (10) provide the capability for end users of the user-interface to dynamically set alert and threshold levels associated with particular data displayed through the interface such that notifications may be communicated both visually and through standard means of messaging from the system to the user should particular relational conditions associated with the data be met.

BRIEF DESCRIPTION OF THE DRAWINGS

The accompanying drawings, which are incorporated herein and form part of the specification, illustrate embodiments of the present invention and, together with the description, further serve to explain the principles of the invention and to enable a person skilled in the pertinent art to make and use the invention. In the drawings, like reference numbers indicate identical or functionally similar elements. Additionally, the leftmost digit(s) of a reference number identifies the drawing in which the reference number first appears.

FIG. 10B shows an example of a library of user definable coded rules.

FIG. 14 shows an example of the user-interface having user comments.

FIG. 17 shows an example user-interface allowing the user to view data and select data manually.

FIG. 21 shows a system architecture 2100 according to aspects of the present invention.

FIG. 22 shows a flowchart of an exemplary method, according to an embodiment.

DETAILED DESCRIPTION

Figure 1:
FIG. 1 shows an example user-interface for selecting patients.

The following Detailed Description refers to accompanying drawings to illustrate one or more embodiments consistent with the present invention. The disclosed embodiment(s) merely exemplify the invention. References in the Detailed Description to "an example embodiment," "an example of this embodiment," etc., indicate that the embodiment(s) described may include a particular feature, device, or characteristic, but every embodiment may not necessarily include the particular feature, device, or characteristic. Moreover, such phrases are not necessarily referring to the same embodiment. Further, when a particular feature, device, or characteristic is described in connection with an embodiment, it is within the knowledge of those skilled in the relevant art(s) to affect such feature, device, or characteristic in connection with other embodiments whether or not explicitly described.

| Table of Contents | |
|---|---|
| 1. | Overview, Features and Advantages |
| 2. | User-Interface Examples |
| 3. | Patient Charting View |
| 4. | Table - Graph Toggling |
| 5. | Time Scaling |
| 6. | Threshold Markers and User-Definability |

| | Table of Contents |
|---|---|
| 7. | User-Definable Rules |
| 8. | Grid View with Alerts |
| 9. | Further Data Options: Selection, Comments, Transmission, and Export |
| 10. | System Environment(s) |
| 11. | Overview of the Method |

1. Overview, Features and Advantages

This disclosure is directed to systems and methods for providing clinical information and clinical analysis (e.g., informatics), and more particularly, systems and methods for providing trending observations, user-defined analysis rules based on any datum, and raw measurements from any data source at a point of patient care. In embodiments, a user-interface and analysis tool for use with existing electronic medical records (EMRs) are provided. The user-interface and analysis tool described herein can operate readily with any biomedical device data, laboratory data, or other discretized data elements to facilitate near real-time trending of observations and raw measurements analysis, threshold notification and data trending right at the point of care.

In this way, according to a further feature, a new clinical informatics system provides the ability to: (i) receive, analyze, and display near real-time data; (ii) plot patient data in tabular and graphical format; (iii) manage alerts and notifications (also referred to as "smart alerts"); and (iv) interact from the perspective of a clinical staff member who can make decisions on the basis of these data. The user-interface is dynamic and flexible, thereby enabling clinical staff to review data more effectively and actively participate in research and analysis. To achieve this, data can be exported at will in formats readily acceptable to existing statistical and analysis packages (e.g.: SAS, SPSS, Microsoft Excel, Matlab, etc.), which is otherwise unavailable through conventional clinical information systems featuring end-user proscribed charting flow sheets. In embodiments, the user-interface can be implemented at any level of the healthcare enterprise: from emergency care settings, surgical services, critical care settings, specialty care (e.g., nephrology and joint replacement), to medical/surgical step-down and ambulatory/home settings. For example, embodiments of the present invention can be used: by an emergency department to, e.g., minimize door-to-balloon time and assist stroke and heart attack victims in a more timely manner; in critical care settings such as detection of sepsis onset and other hospital acquired infections (HAIs), measurement of intracranial pressure, bed headboard management (i.e., an angle of the head of bed, which is critical for patients, particularly when receiving mechanical ventilation), and weaning patients from post-operative mechanical ventilation; for use in medical/surgical step-down environments, such as for rapid response team notification and sepsis onset as well as thirty day re-admission/congestive heart failure patient assessment; and in ambulatory (or home) settings to facilitate chronic disease management monitoring.

Embodiments described herein advantageously provide, for example:

The display of the vitals data in a columnar charting format consistent with visualizations employed by clinical staff, which provides the capability to show a minimum of 24 hours of data on any patient in the span of the eye, e.g., on a single screen.

The display of vitals data, which can be tailored to support the needs of individual users, e.g., tailoring of the view can be saved as a preference for each user.

Users can interact with tools and change the view in real-time using, for example, a web-based interactive tool developed using a markup language, such as HTML-5, to enable modification of the view.

The capability to validate a specific columnar set of data so that results which meet with clinical approval are transmitted to a clinical information repository, such as an electronic medical record or clinical information system using a standard such as Health Level Seven (HL7) unsolicited observation reporting.

The ability to set parameter-level thresholds on individual parameters to facilitate event reporting when certain values exceed a predetermined threshold, thereby providing the capability to manage medical device data and patient observations dynamically. The thresholds can be tailored to clinical needs of the end user as per the practice of medicine, to minimize the occurrence of "nuisance" alarms.

The ability to combine multiple sources of data into complex rules structures using a rules engine configured to enable the creation of the rule structures using a scripting language. The rules can be based on multiple sources of data and defined by the needs of the clinical end user to develop alerts and notifications as desired and needed for each patient to facilitate early warning notifications (e.g., smart alerts) of specific events based on the trends of particular data versus the occurrence of an event.

The ability to create and manage rules to operate on the real-time collected data and provide notifications on the basis of conditions specified by the thresholds and/or rules, either when certain thresholds are "tripped" or when collected data "approach" or trend towards a particular threshold.

Tools to calculate and display parameter minimums, maximums, averages, deviations, modes, and to apply other statistical tools to evaluate the data presented to the user.

The ability to graphically select a subset of data within the user-interface so that a user can "grab" the data for quick analysis.

As a result, client needs such as connectivity requirements, high acuity, integration interface particulars with electronic health records (EHRs), documentation and reimbursement requirements, patient safety and hazard mitigation, and established workflow practices can be addressed according to aspects of the present invention. In embodiments, the present invention can be used, for example, to help prevent patient deaths due to opioid respiratory insufficiency, to monitor pre-discharge infants for apnea and/or cardiovascular function, monitor children at home receiving pain medication or bi-level positive airway pressure (Bi-PAP) therapy, and monitor children during transport to and from the intensive care unit. It should be understood that these uses are only examples and that other uses are also contemplated by the present application. Further examples are illustrated in the figures below.

Additional features include the capability to visualize twenty-four (24) hours of medical device data on a patient collected through a data management system, with the option to extend the monitoring indefinitely for any duration of patient length of stay at any level of data granularity, up to and including high-frequency data collection such as waveforms. For example, according to aspects of the present invention, a visualization and validation tool, and a platform for data analytics, e.g., an analytics platform can be provided. In embodiments, further features include the capability to transmit data manually or automatically to electronic medical records (EMRs) or other end-point clinical information systems using Health Level Seven (HL7) results transactions in text or XML format.

In embodiments, patient identification can originate with a hospital master patient registration system (e.g., an EMR). In embodiments, locations of monitored patients can be determined per the procedure established for device managers utilized by a particular patient. As a result, knowledge of the medical device, patient demographics, patient and medical device location can be provided to a user. Furthermore, data can be displayed in a synchronized, columnar format that aligns the time stamps of all findings from potentially disparate sources associated with the same patient (i.e., different medical devices associated with the same patient but that are collecting data independently) in a visual display at a point of care regardless of data source (i.e., from a variety of medical devices).

In embodiments, different classes of users can access the systems described herein, for example, clinical users and non-clinical users (e.g., individuals associated with biomedical or clinical engineering or health information technology departments). Clinical users can include physicians, nurses, and respiratory therapists. It should be understood by those of ordinary skill in the art that the types of clinical users are only illustrative and that other types of clinical users are further contemplated according to aspects of the present invention. In embodiments, clinical users can have role-based functional capabilities and notifications can be provided to each individual user based on their role. The clinical users can have the ability to view, select and transmit patient device data to the EMR. In embodiments, clinical users can have access to a "Domain" that specifies the hospital system to which the clinical user has access and does not have any restrictions on date/time for clinical access. Furthermore, the clinical user's home page can contain their patient assignments and display icons next to each patient for their devices/templates/charts. These charts can display a status of patient device data capture, and acceptance and transmission to EMR with its color representing the data "state" (e.g., data are transmitted or not transmitted-akin to clinical validation).

In embodiments, IT users can have access to both the data management system and the systems described herein. That is, IT users can access templates and patient charts and the data management system. The IT users can also receive notifications when a medical device malfunctions or data is not properly transmitted to an EMR. It should be understood by those of ordinary skill in the art that additional classes of users are further contemplated according to aspects of the present invention.

According to aspects of the present invention, the systems described herein can be used for data collection, storage and clinical information management from bedside and independent point of care biomedical devices. In embodiments, clinical information management systems can be accessed either directly or through networks with medical devices. Additional advantages include the capability to provide patient information and surveillance of monitored patients at the point of care location and at a remote supplementary care location through networking technology. In embodiments, physiologic data and other patient information can be displayed to and used by clinicians to assist with diagnostic aid.

In embodiments, the user-interface can be a web-based application that allows the display of patient monitoring data aggregated from a data management system in user-defined formats. In embodiments, the user-interface can be accessed via a dedicated URL. In embodiments, the user-interface can be web-based and accessed from any web browser. In one example, not intended to be limiting, a browser can be used that supports drawable regions defined in HTML code with height and width attributes that allows for dynamic, scriptable rendering of 2D shapes and bitmap images, such as, canvas elements in HTML 5. In embodiments, the user-interface can be accessed on any computing device, e.g., a smartphone, tablet PC, laptop computers, etc. In embodiments, the user-interfaces described herein can be shown on a web-browser using a computing device 2008 as described with respect to FIG. 20 discussed below. In embodiments, the user-interface can be generated using a server, e.g., XML-RPC server 2006 of FIG. 20. That is, a server can collect device from an array of sources, e.g., medical devices, hospital records, etc., and generate user-interfaces 100-1800 shown in FIGS. 1-18. In this way, user-interfaces shown on computing device 2008 can be generated by XML-RPC server 2006.

In embodiments, context management and single sign on procedures, e.g., CCOW and SSO, can be utilized. The data management system can be configured to permit data from bedside and point of care medical devices to be aggregated and transmitted to the hospital health information technology or electronic medical record systems. In embodiments, data collected by the data management system from the bedside monitors at discrete time points can be displayed to the user. In this way, the embodiments of the present invention can be used by clinicians as a diagnostic aid. For example, in embodiments, the present invention can be used in the following roles:

Data validation tool—Users can view the data from the bedside monitoring devices, and use the system as a validation tool for transferring data to EMRs.

Trending tool—Users can view a summary table and/or graphic representation of the data over time.

Notification tool—Users can define rules and thresholds where certain conditions will prompt an alert to be sent to a designated individual.

2. User-Interface Examples

Upon logging on, a user can be presented with a patient selection screen, e.g., user-interface 100, as shown in FIG. 1. From here, a user can select patients to be monitored from a list of patients connected through the data management system. In embodiments, the user can also select data to be displayed for each patient using a patient selector portion 102. For example, a clinical user can view a list of patients, and filter patients by department/unit or search for a specific patient name. In embodiments, a list of assigned patients and patient charts are a clinical user's home page until the clinical user changes patient assignments. In embodiments, for patient data to be shown, the patient should first be associated with a medical data collection appliance or be receiving data from an existing medical device data system (MDDS), and all device data they are collecting. In embodiments, an association with a medical data collection appliance can occur using a barcode scanner, or an "admission, discharge, transfer" association of a patient to a bed. A bed ID can then transformed and displayed with another identifier (e.g. birthdate, bed/room location/MRN) as confirmation.

Data can be presented in categories, or groups of data points associated with a device "category." Examples of device categories include but are not limited to: pumps, patient monitors, mechanical ventilators, ad-hoc spot vital signs machines, glucose meters, and any other type of medical device that transmits patient data. In embodiments, data relevant to the clinical user's decision making and patient assessment can be displayed. For example, patient demographics, device data, date/time, device category, device name, validation status and menu system can be displayed to the clinical user.

3. Patient Charting View

Figure 2:
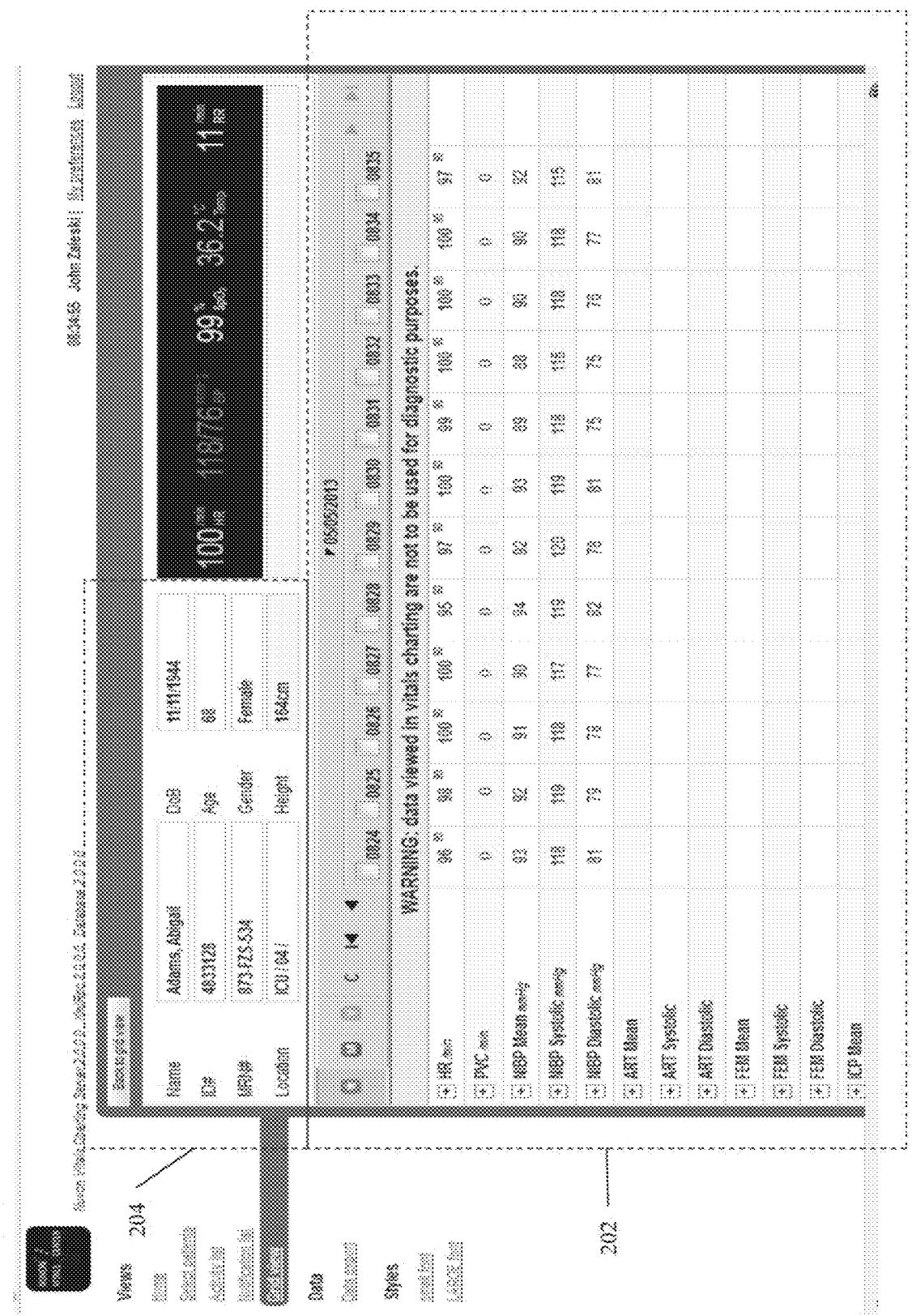
FIG. 2 shows an example of a user-interface with a patient charting view.

FIG. 2 shows an example of a user-interface 200 having a patient charting view. In embodiments, the patient charting view shows parameters in a tabular format 202. For example, each row lists a parameter obtained from the bedside monitor and each column identifies a common reporting time interval associated with the listed parameters, propagated to the nearest reporting time. For example, as shown in FIG. 2, the parameters can include heart rate ("HR") and premature ventricular contraction per minute ("PVC/min") among others. In embodiments, a "[+]" symbol next to each row provides the ability to expand the tabular cell value into a graphical trend. The user-interface of FIG. 2 also includes a patient data portion 204, which can include a patient's name, ID number, location, date-of-birth, age, gender, and height. It should be understood by those of ordinary skill in the art that other patient data and parameters can be displayed.

4. Table—Graph Toggling

Figure 3:
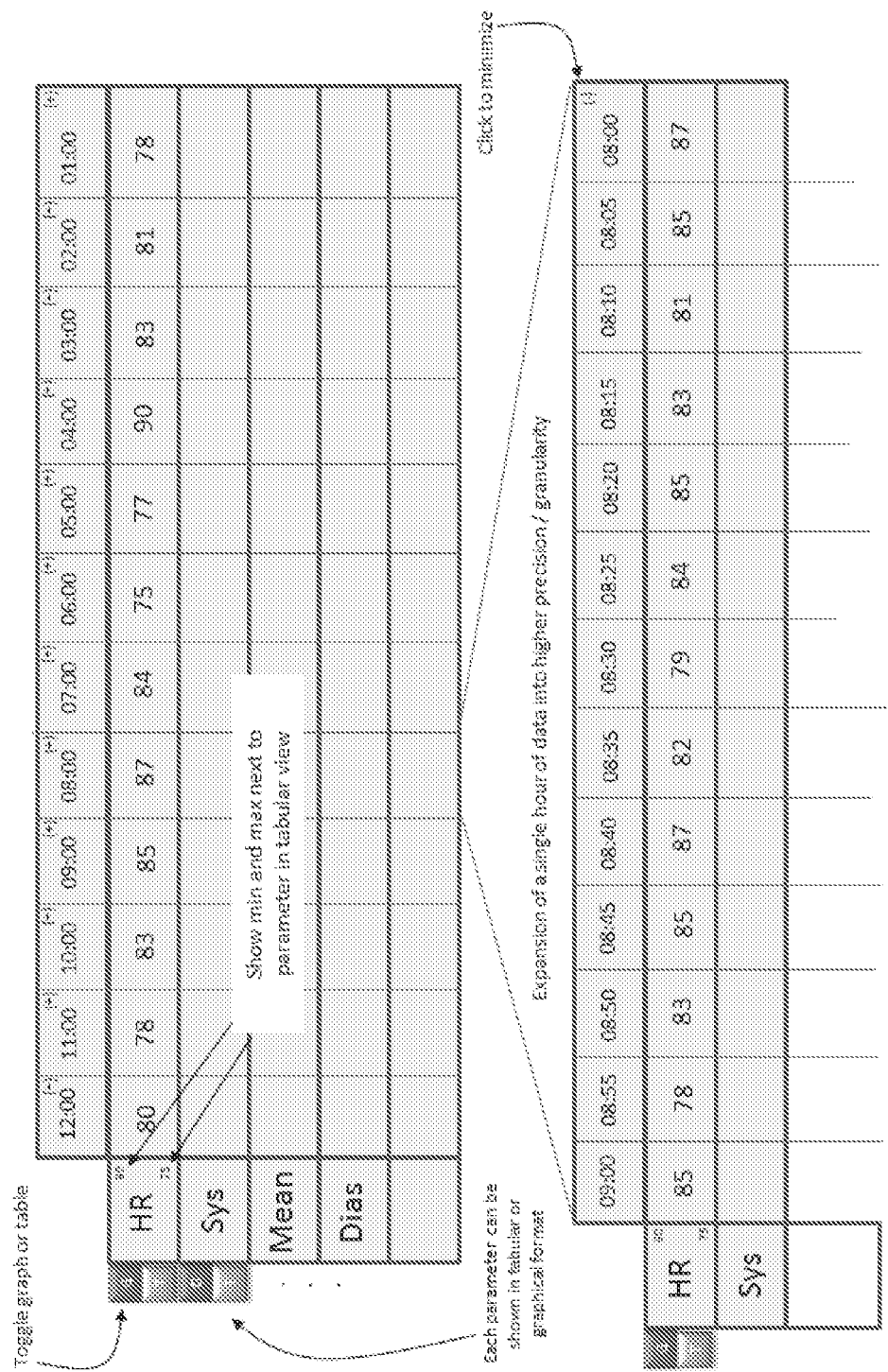
FIG. 3 shows an example user-interface.

FIG. 3 shows an example user-interface 300 according to aspects of the present invention. FIG. 3 shows a plurality of parameters, for example heart rate ("HR"), systolic blood pressure ("Sys"), mean blood pressure ("Mean"), and diastolic blood pressure ("Dias"). In embodiments, these parameters can be grouped according to a physiological system. In addition, a tabular view or a graphical view of data can be selected at the touch of a toggle button ("G"=graphical; "T"=tabular). As further shown in FIG. 3, minimum and maximum values can be displayed concomitantly with the tabular data. In embodiments, the minimums and maximums are displayed as small text within the cell containing the name of the parameter.

Furthermore, according to aspects of the invention, time scaling of each column can be expanded or collapsed. Clicking on the "+" symbol shows a higher granularity of data for a given parameter, e.g., five minute intervals. Thus, expansion of a particular hour of data can be expanded into higher precision/granularity of time. The level of granularity can be collapsed by clicking on the "−" button. In this way, tabular graphics which can be expandable to a lowest level of granularity, or collapsible to a "big picture view."

5. Time Scaling

Figure 4:
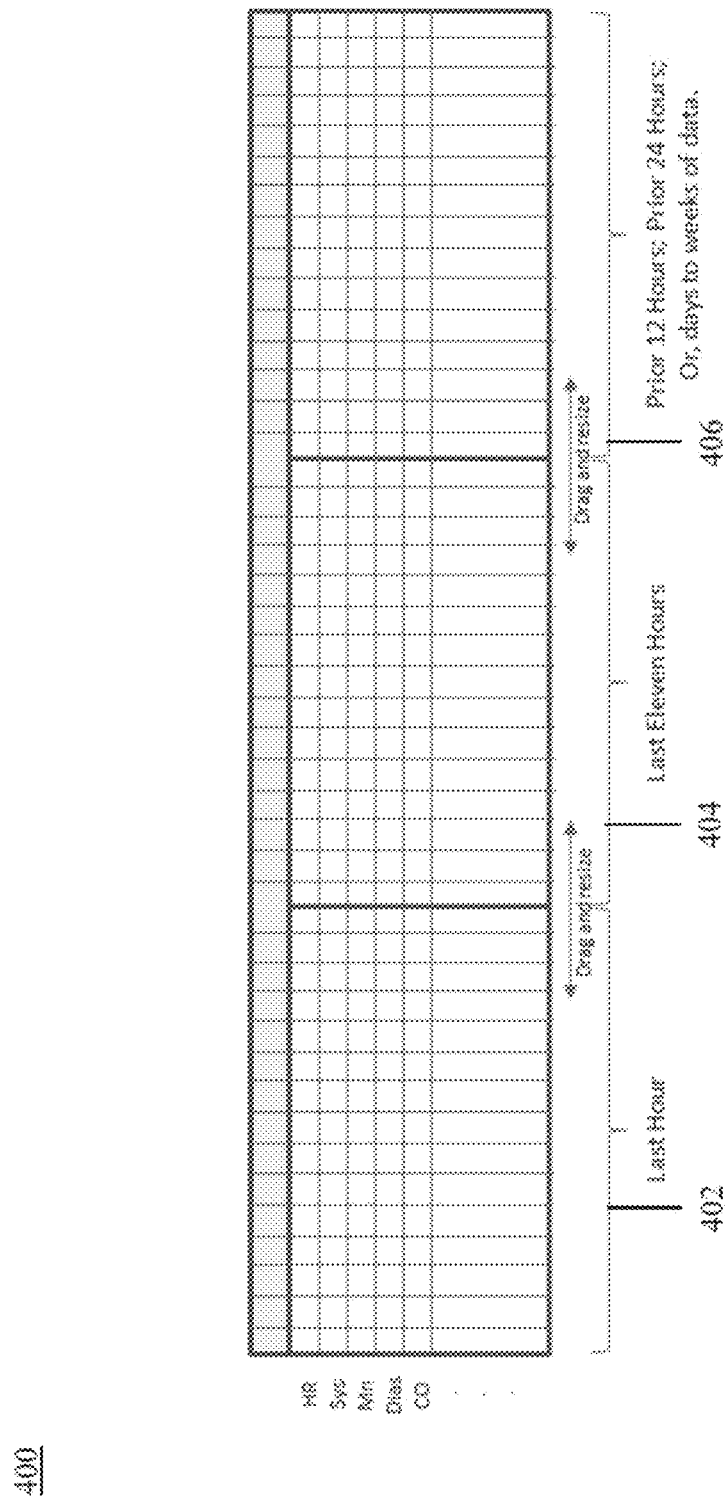
FIG. 4 shows an example of a user-interface using time scaling.

FIG. 4 shows an example of a user-interface 400 using time scaling. In embodiments, most recent data can be presented in high detail close to the current time. For example, FIG. 4 includes three phases: the left-hand phase 402 showing a most recent hour of data; a middle phase 404 showing a prior 11 hours of data; and a right-hand phase 406 showing data prior to 12 hours preceding. It would be understood by those of ordinary skill in the art that alternate time frames for each of the phases 402-406 are further contemplated according to aspects of the present invention. For example, in embodiments, the right-hand phase 406 can include data from days or weeks of information, but can be compressed and presented in a coarse format. The time scaling windows can be dynamically resized by the user. In embodiments, the time can be a log-linear. For example, time nearest a current time can be shown linearly, i.e., in phase 402, with times farther away, e.g., 12-24 hours, i.e., phase 406, being compressed to show a "full picture." In this way, the user-interface provides for the capability to produce log-linear graphics such that newer data is shown in full and older data can be compressed.

Figure 5:
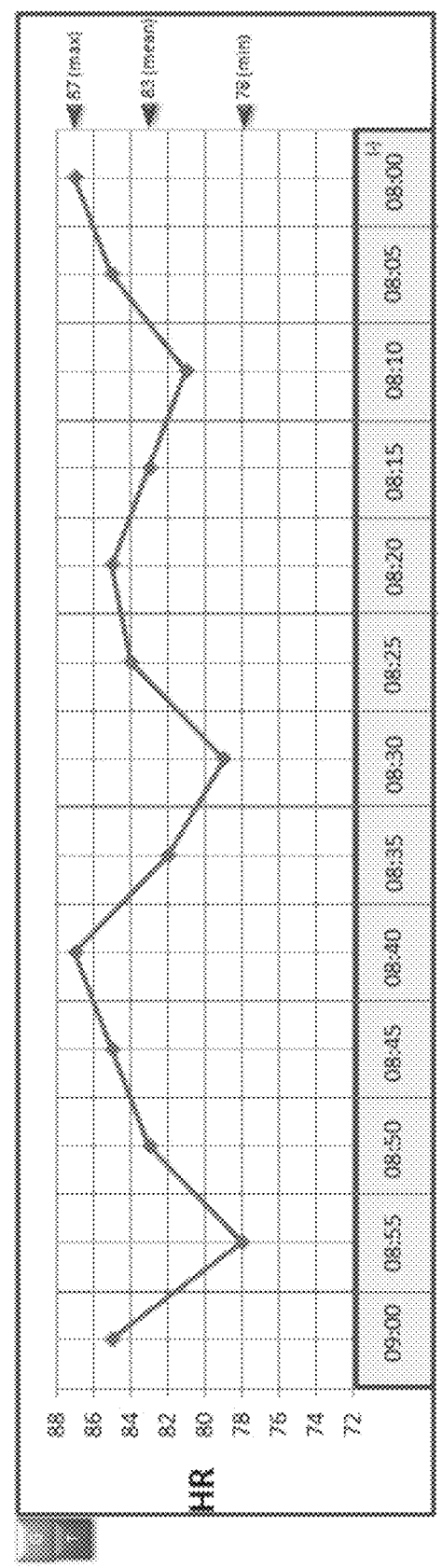
FIG. 5 shows a user-interface toggled to a graphical display view.

FIG. 5 shows a graphical display 500 when the user-interface is toggled by pressing the "G" button as shown in FIG. 3. Upon pressing the "G" button, a set of values from the tabular view can be displayed as a graphical plot for a selected parameter, e.g., a heart rate. The graphical plot of FIG. 5 shows a time scale with a higher granularity as described with respect to FIG. 3. In embodiments, arrows can be displayed to indicate maximum, mean and minimum values. Additionally, in embodiments, the time scale can be displayed as described with respect to FIG. 3.

6. Threshold Markers and User-Definability

Figure 6:
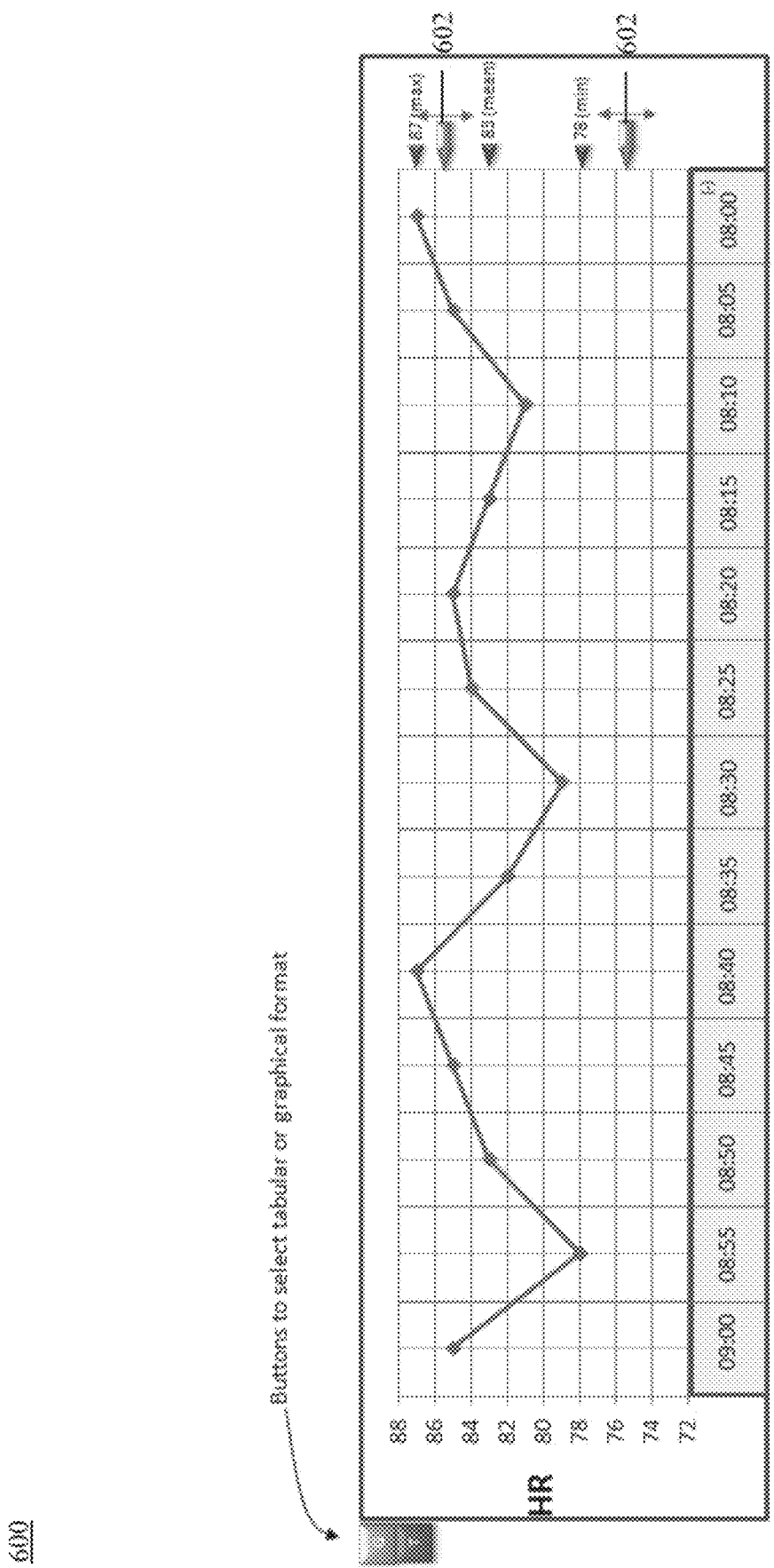
FIG. 6 shows an example of a user-interface having threshold markers.

FIG. 6 shows an example of a user-interface 600 having threshold markers. For example, threshold markers, e.g., markers 602, can be used to represent thresholds values, e.g., maximum and/or minimum values, which can be set by a user. In embodiments, when values exceed or fall below these threshold markers 602, a resultant event action can be used to trigger notifications, e.g., an email, page, audible notification etc., to a clinician. In embodiments, these threshold markers 602 can be draggable, i.e., moved to a particular value, as indicated by the vertical arrows adjacent to threshold markers 602. The threshold markers 602 can also be tied to triggers that can be reported through medical device integration (MDI), nurse call system, EHR dashboard or other notification systems, such as, pagers, e-mail, audible notifications, etc., when the threshold markers are exceeded.

Figure 7:
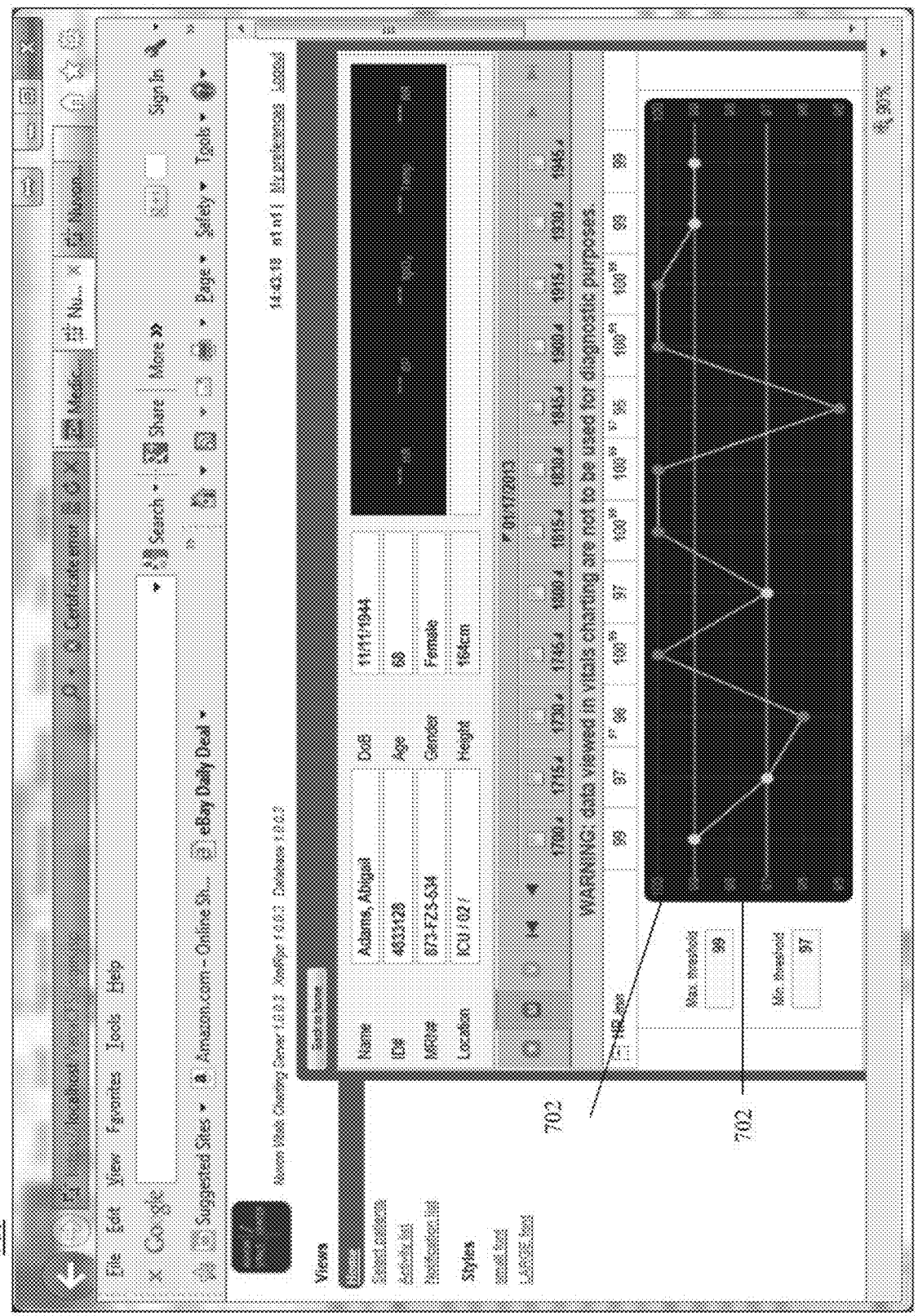
FIG. 7 shows a graphical display having user defined thresholds.

FIG. 7 shows a graphical display having user defined thresholds. In embodiments, the user-interface allows the user to set various parameters for evaluating trends in a patient's data. The thresholds may be set on any finding (i.e., observation or parameter). In embodiments, users can enter thresholds on individual parameters, and can later be modified. For example, as shown in FIG. 7, a maximum threshold value for a heart rate is 99 bpm (beats per minute) and a minimum threshold value is 97 bpm. In embodiments, the threshold levels can be marked using horizontal lines 702 on a graphical plot. Furthermore, any data points exceeding the threshold values can be marked using a first colored data point, e.g., red, whereas data points within the threshold values can be marked using a different colored data point, e.g., green. It should be understood by those of ordinary skill in the art that other markers can be used for the data points, e.g., data points exceeding the threshold values can be marked using different shapes such as an "*" symbol or a "+" symbol.

Figure 8:
FIG. 8 shows a template for modifying a threshold value for a selected parameter.
Figure 9A:
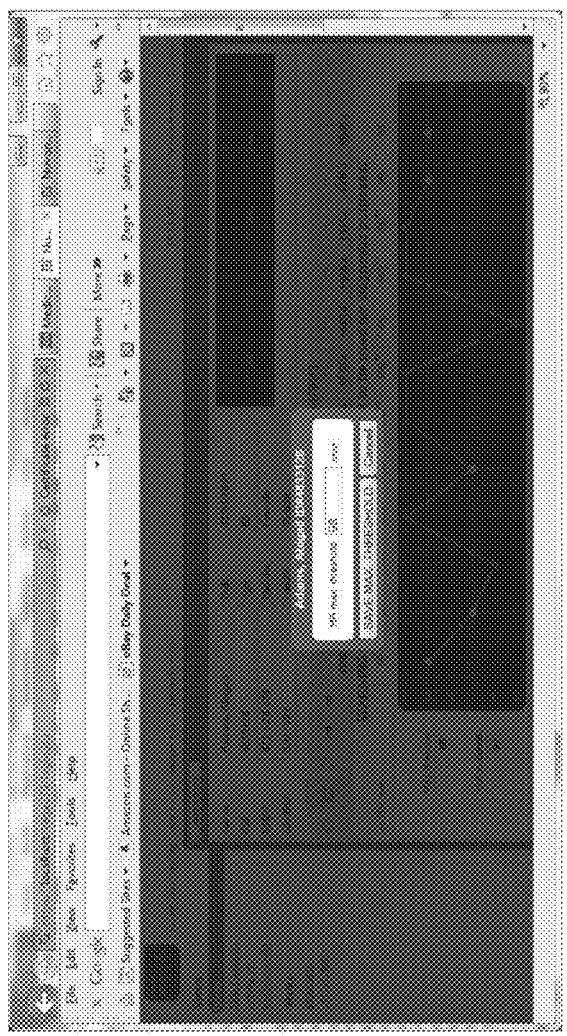
FIGS. 9A and 9B show editor pop-ups for modifying a threshold value.
Figure 9B:
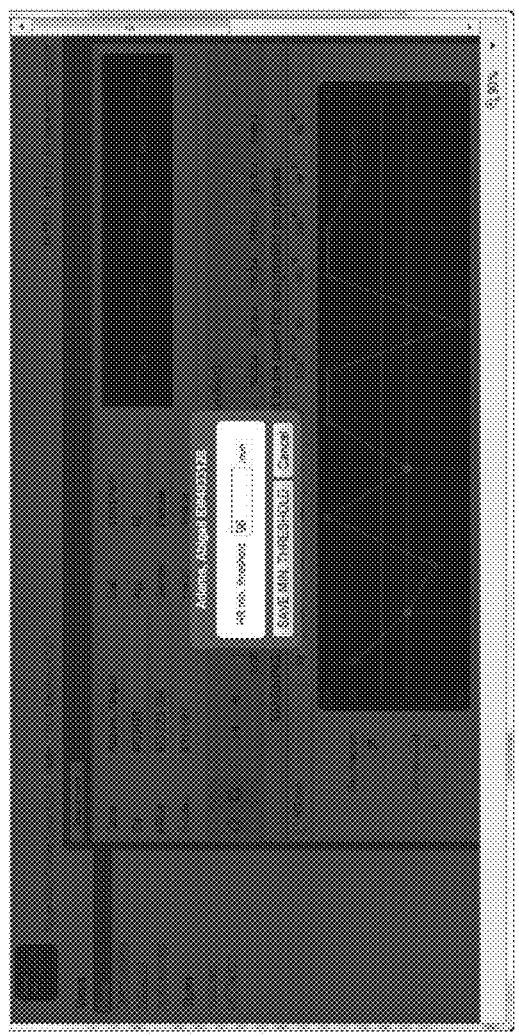

In embodiments, a threshold value for a selected parameter can be modified using a template 800 as shown in FIG. 8. Using the template 800, a user can define threshold minimum and maximum values. Alternatively, threshold values can be modified by clicking on a desired threshold, e.g., maximum value or minimum value, which can cause an editor window to pop-up. For example, clicking a maximum threshold for HR brings up the editor window, as shown in FIG. 9A, where the user can edit or override the previously defined value. Similarly, clicking the HR minimum threshold, as shown in FIG. 9B, brings up an editor and the user can define a minimum threshold value. Upon saving the new maximum and minimum threshold values, each data point beyond the maximum and minimum threshold values can be showing using a colored data point or different shaped data point. Additionally, data values exceeding the threshold values can be shown in the data cells, e.g., as red bold text on the tabular layout in the upper right corner of data cells.

The display of the patient data collected from bedside monitors is viewed in tabular form and the display screen allows the user to define thresholds upon which notification alerts can be generated. The user can set individual minimum and maximum parameter values in defined thresholds. Upon entering a value, the user will be prompted to save that setting. Upon saving, a visual line indicator of the threshold value appears on the graphical plot. If the plotted signal exceeds (or falls below) the threshold, a notification is transmitted to whomever is identified to receive the notification setting. When thresholds are exceeded, visual indications of these events are provided in the user-interface in both graphical and tabular format. An example showing the visual indication as a series of red points above a threshold, in which the example parameter, heart rate (HR), is shown to exceed a user-defined threshold.

In embodiments, further advantages include the capability to communicate value of parameters in relation to an associated threshold. That is, in embodiments, where a plurality of proximal threshold levels correspond to levels of notification can be defined. For instance, a heart rate can have a "not-to-exceed threshold" (NTE threshold) set for 120 bpm, which identifies point at which a "red" notification can be transmitted to one or more specified users. Furthermore, an "intermediate threshold" (IT threshold) can be set to 90 bpm, which identifies the point at which a "yellow" notification can be transmitted to the one or more specified users. In embodiments, the "yellow" notification represents a default and the coloration of notifications can be custom tailored to enable any possible coloring scheme associated with various threshold levels. In embodiments, notifications can be sent when the IT threshold is triggered and when the NTE threshold is triggered. In this way, the one or more specified users can be aware of trending vitals of a patient, such that they can take preventative actions or be on alert of a patient's condition. In embodiments, the notifications transmitted for the IT and NTE events can include the values of the specific parameters (or rules) displayed in the notification as well as a color metaphor indicating the occurrence of IT and NTE events.

FIG. 7 also shows a user-interface having minimum and maximum threshold level indicators in the content of each cell. In embodiments, minimum thresholds are shown in the top left-hand side of each cell and maximum thresholds are shown in the top right-hand side of each cell, respectively. In embodiments, a most recent value obtained from the patient monitor (centered in cell), a minimum threshold (top left), and a maximum threshold (top right) can be displayed within the cell and when a threshold is exceeded, the cell with an out-of-range value is colored, e.g., red.

7. User-Definable Rules

Figure 10A:
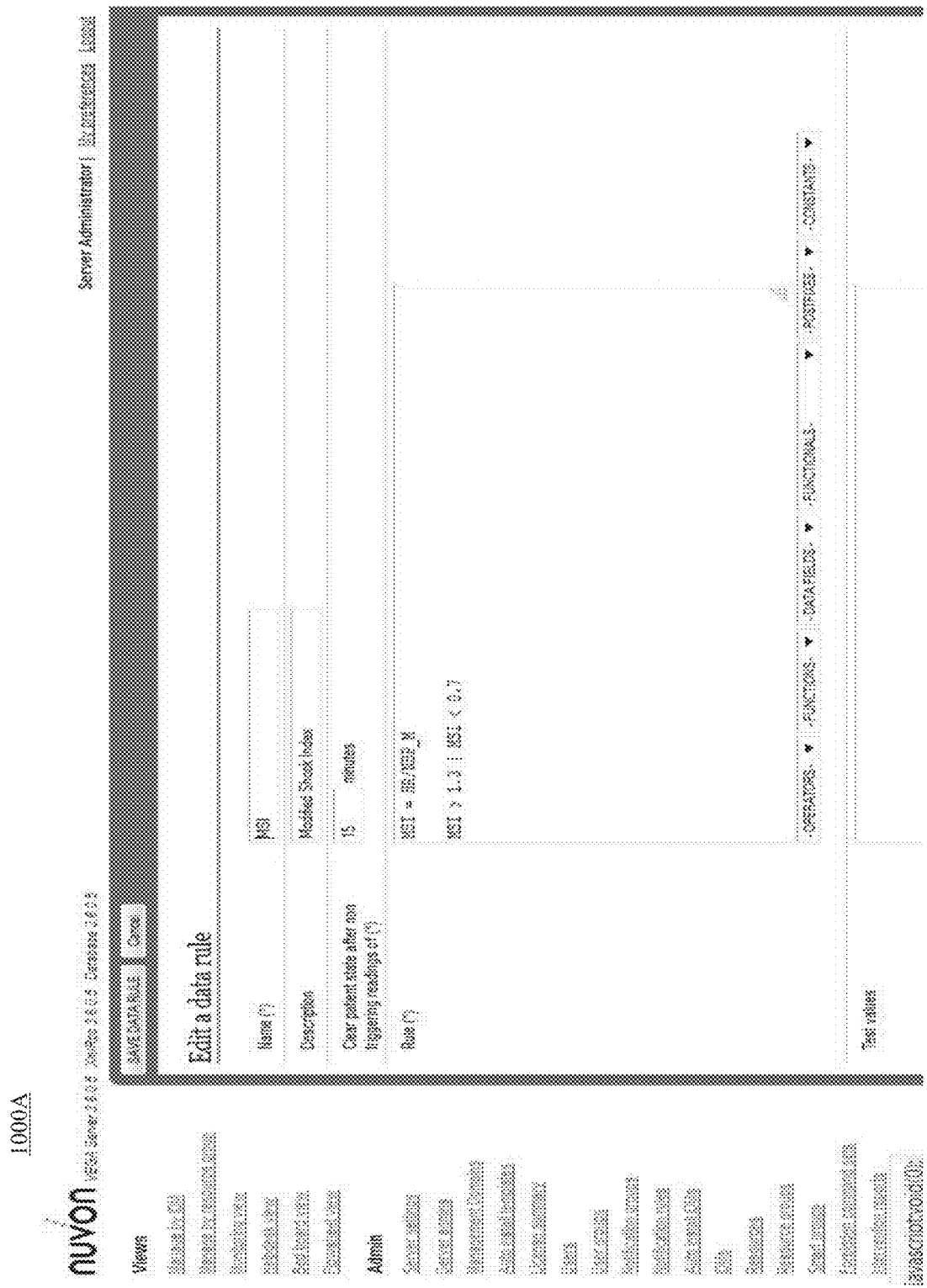
FIG. 10A shows an example user-interface having user definable coded rules.
Figure 10B:
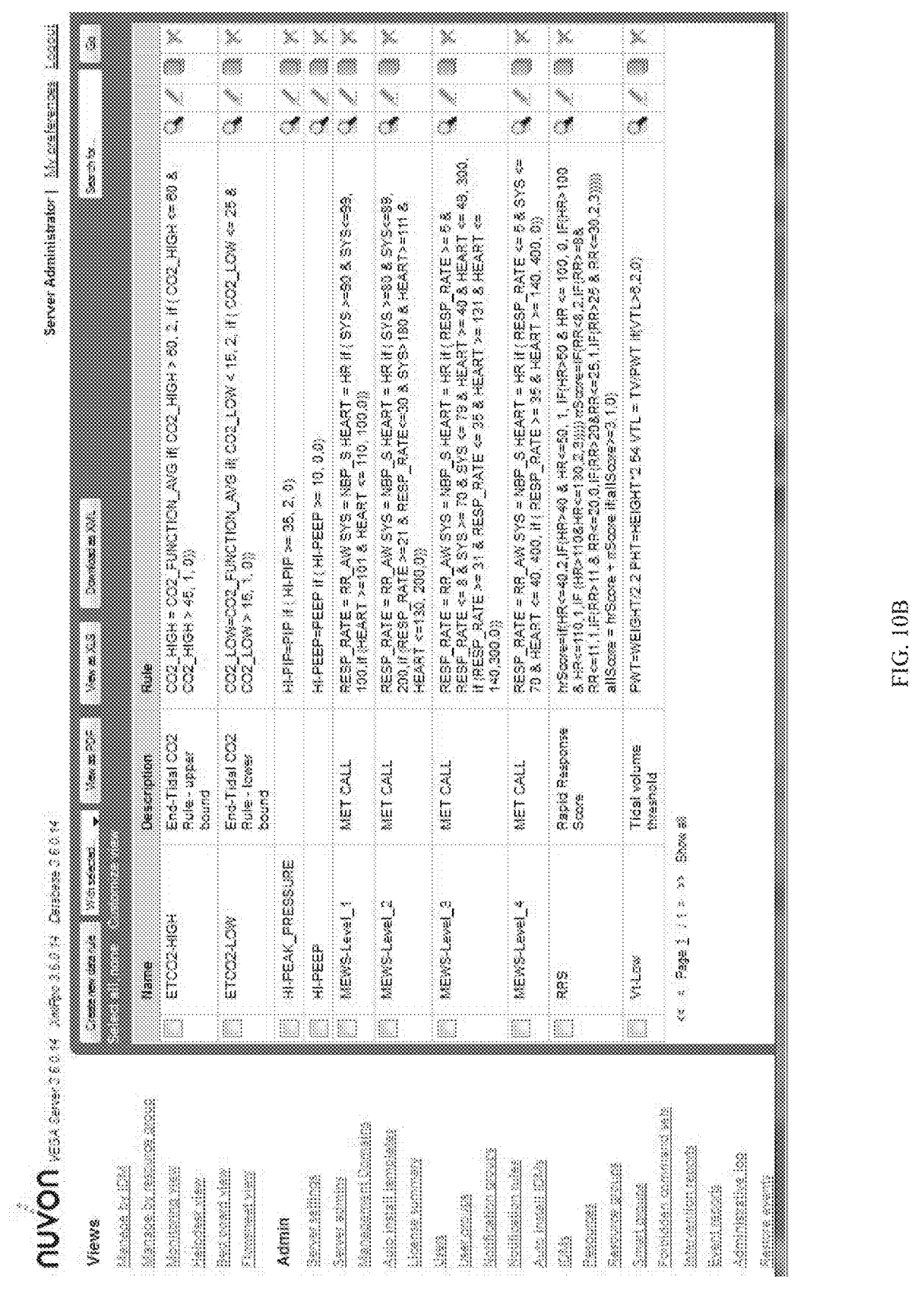

FIG. 10A shows an example user-interface 1000A having user definable rules according to aspects of the present invention. In embodiments, rules based on individual or combined medical device parameter values per patient or a collection of patients can be created by a user. FIG. 10B shows a library 1000B of user-definable rules that can be applied to any patient based upon rules and notifications settings established by the user. FIG. 10A shows a user-interface configured to permit a user to define rules for a specified parameter. In embodiments, rules (and thresholds) can be tailored to a specific patient or a specific department. For example, as shown in FIG. 10A, a user can define thresholds for a modified shock index ("MSI") such that the user can be notified when the MSI exceeds the thresholds.

Another example rule can be based on capnography. More specifically, the rules can be written to monitor the interplay between a patient and an anesthesia administration device, e.g., which is usually a breathing circuit and a ventilator, when anesthesia is being administered, or to monitor the administration of opioids.

In embodiments, rules can be simple mathematical expressions and conditions that can be defined and stored by the user. These rules can be applied to parameters or medical devices such that the user is notified upon occurrence of a condition defined by the rule. That is, the rules can be stored or recalled, and used to send a notification when specified conditions are met. The rules can be set to provide a notification when conditions related to a medical device, e.g., when a medical is turned off/on been disconnected, or placed in a specified operating mode based on the available data delivered by the point of care medical devices through the medical device collection appliances. The rules can also be set to send a notification based on one or more parameter observations received from the medical devices. In embodiments, users can create, apply or cancel rules at will. Additionally, the ability to create a new rule and change the rule's contents can be limited on the basis of the user (i.e., role-based access to rule changes). The ability to modify threshold values can be similarly limited on the basis of the user.

The triggered notifications can be provided to a pre-identified stakeholder(s), such as a clinical user (e.g., an attending physician) or group of clinical users (e.g., a rapid response team). These identified stakeholders can be specified by the rule creator when the rule is first written or later modified to change the stakeholders. In embodiments, the notifications sent to the user can be generic notifications that a rule or threshold has been triggered, or alternatively, the notifications can provide specific details including the rule and/or threshold and the data which caused the rule/threshold to be triggered. Additionally, either of these notifications can include a link which provides data detailing the precise circumstances at the time the notification was triggered.

In embodiments, the user can enter a rule in a pseudo-code format, e.g., using a scripting language. For example, the rule syntax can include conditional logic functions in which parameter expressions such as mathematical relations (*, /, +, −, %) and conditional expressions (<, >, <=, >=), which can be combined to assess the interrelationship among one or more parameters. Additionally, the user can name and label the rule for later recall. In embodiments, the rule can saved and stored by pressing a "save" button. After a rule has been saved, the user new rules can create additional rules by pressing the "new" button. In embodiments, saved rules can be activated or deactivated by clicking an activation box next to each rule. In embodiments, the rules can trigger notifications as described with respect to threshold values. In other words, the rulers operate in the similar way as threshold expressions, e.g., when bounds of a rule are exceeded, a notification is displayed and communicated to the end user. In embodiments, thresholds and rules can be combined to provide additional notifications to the user.

In embodiments, a user can access tools through pull-down menus in order to create the rules as desired. For example, as shown in FIG. 10A, a user can be provided with "operators," "functions," "data fields," "functionals" (e.g., user-defined statistical functions associated with individual data elements, such as mean heart rate or standard deviation in respiratory rate), "postfixes" (e.g., such as _EXISTS or _NOW denoting elements defining the existence or state of being of a particular data element), and "constants" pull-down menus. The "postfixes" pull-down menu can include timestamp and date selection options, which can be used when existence of data depends on a time component, e.g., "does the data element exist at specified time?" In this way, the user may create conditional events based upon the time of the data. The "operators" pull-down menu can include mathematical relations, e.g., *, /, +, −, %, and conditional expressions, e.g., <, >, <=, >=). The "functions" pull-down menu can include mathematical functions, e.g., ABS(x) (absolute value of 'X'), as well as other mathematical functions. The "constants" pull-down menu can include mathematical constants such as Pi. The "data fields" pull-down menu can include any data related to the patient, e.g., age, height, sex, blood pressure, etc., as well as data related to a medical device associated with the patient. That is, the parameters associated with the rule are based upon those collected from the bedside medical devices and the patient. The pull-down menu shows all parameters and data fields available to the end user to create a simple or complex rule.

Thus, complex mathematical expressions can be created using algebraic operators as well as other forms of mathematical selections. These mathematical expressions can take on the algebraic manipulations of data through addition, subtraction, multiplication and division as well as complex mathematical structures. In embodiments, the rules can be used to specify when calculations are to be made (i.e., a specified time range) and how often the calculations are updated. Additionally, the rules can be used to modify code books to specify a unit of measure for a particular parameter.

In embodiments, user defined rules and thresholds can be assigned a numeric value. In embodiments, the numeric value can be a default value or a user-defined value. The numeric values can be compared to determine which notification should be sent to the user or shown on the user-interface. In this way, a rule and/or threshold having a higher numerical value can be prioritized and sent/shown to the user.

In embodiments, an exact value of the parameters for which a threshold or rule was exceeded can be communicated to a user. That is, the value threshold and the value of the parameter(s) or rule output can be communicated in a same notification message. Additionally, a visual icon indicating the relative value of the reported parameter in relation to a threshold can be communicated. For example, a red icon can communicate visually the value exceeding a value threshold. In embodiments, an audible alert can be generated when alert notifications occur. For example, a user may set a first audible notification for a low-level alert, a second audible notification for a mid-level alert, and so on. Furthermore, a user can upload audible files to be used as the audible alerts.

8. Grid View with Alerts

Figure 11:
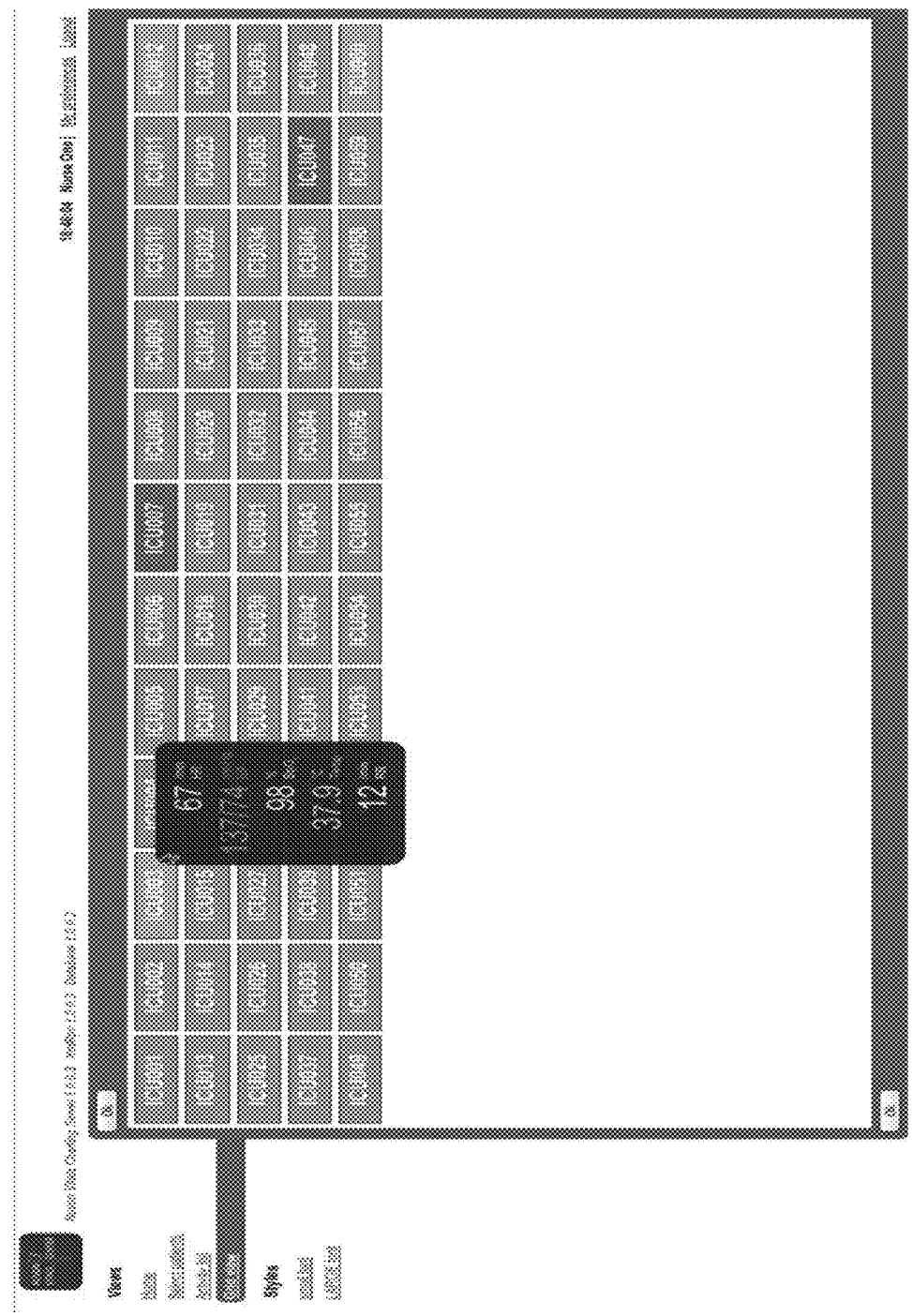
FIGS. 11 and 12 show a user-interface having a grid view of patient locations.
Figure 12:
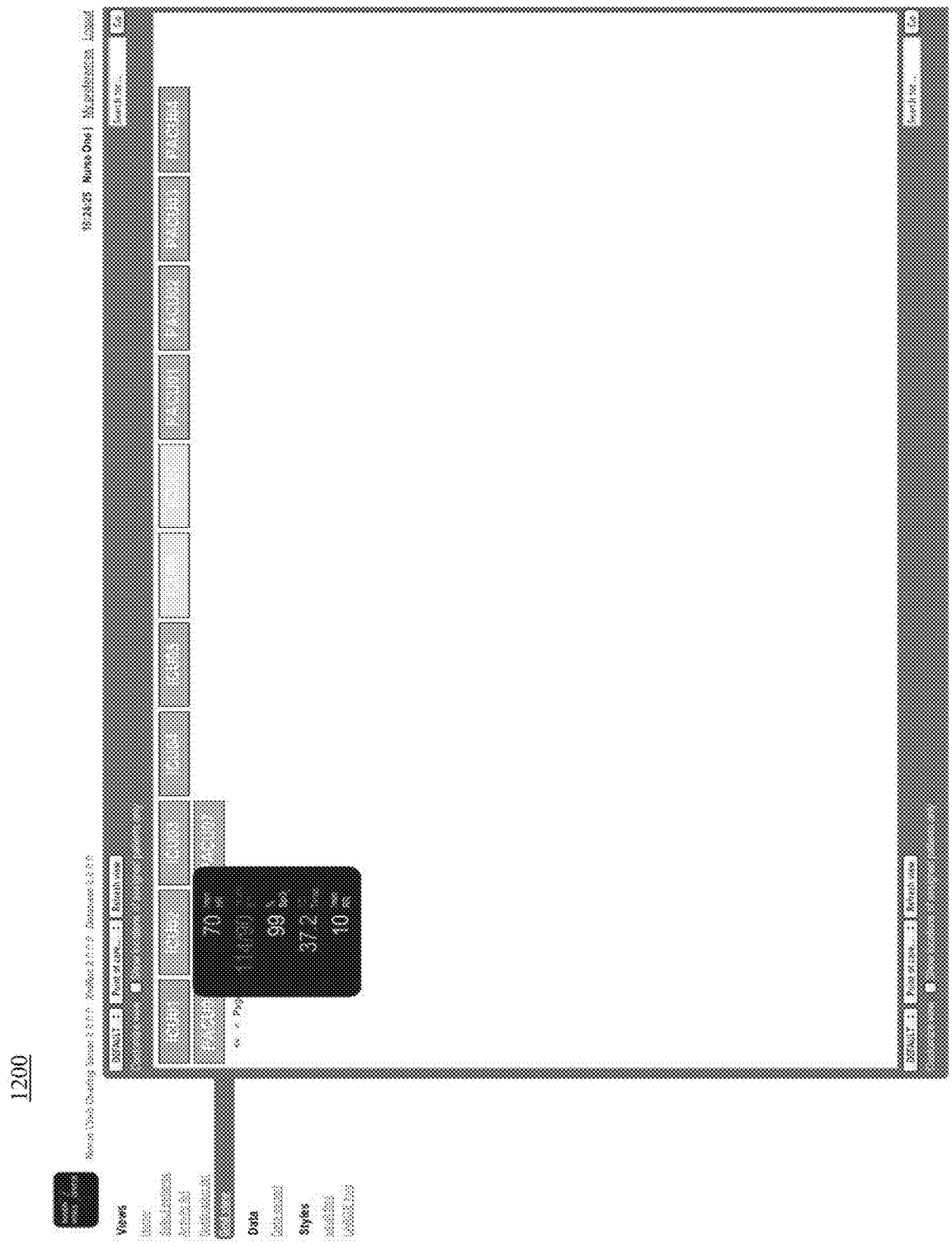

FIG. 11 shows a user-interface 1100 having a grid view according to aspects of the present invention. In embodiments, a grid view can be provided at a census level within the user-interface that can show all patients with respect to given thresholds. In other words, FIG. 11 shows user-interface 1100 having dashboard view of the overall patient population with respect to established thresholds as described herein. In embodiments, alerts having a specified color associated with a threshold can be displayed in the grid view. For example, patients having acceptable readings can have a first colored block, e.g., green, patients with an intermediate alert can have a second colored block, e.g., orange, (patients ICU003, ICU012, and ICU060), and patients with a high level alert can have a third colored block, e.g., red (patients ICU007 and ICU047). In addition, locations without patients can be shown as a fourth colored block, e.g., grey. In embodiments, a user can opt to "show locations of assigned patients only" as shown in FIG. 12. As a result, the grid can remove empty locations and hide locations having patients assigned to other users. In this way, locations assigned to a particular user can reside on the user's home. Coloration of the grid tiles is also customizable to create tailored displays based upon different types of alerts and notification levels to delineate clinical alerts from other types of alerts (e.g.: technical alerts, such as the state of a medical device).

In embodiments, on-mouse-over of a particular patient tab, a patient's clinical information can be displayed as a pop-up. For example, as shown in FIG. 11, vitals data of patient ICU003 can be displayed when a mouse is played over the block corresponding to such patient. In embodiments, statistics shown in the vitals popup can be "clickable" such that clocking on a statistic can take you directly to the acceptance UI for the patient on that location zooming on the time of the particular event or zooming down on current vitals. Patient and user information can also be displayed optionally on the grid tiles to provide identification of the particular patient within the eye span of the user without requiring a drill-down into the particular grid element, thereby negating the need for additional mouse clicks.

9. Further Data Options: Selection, Comments, Transmission, and Export

Figure 13:
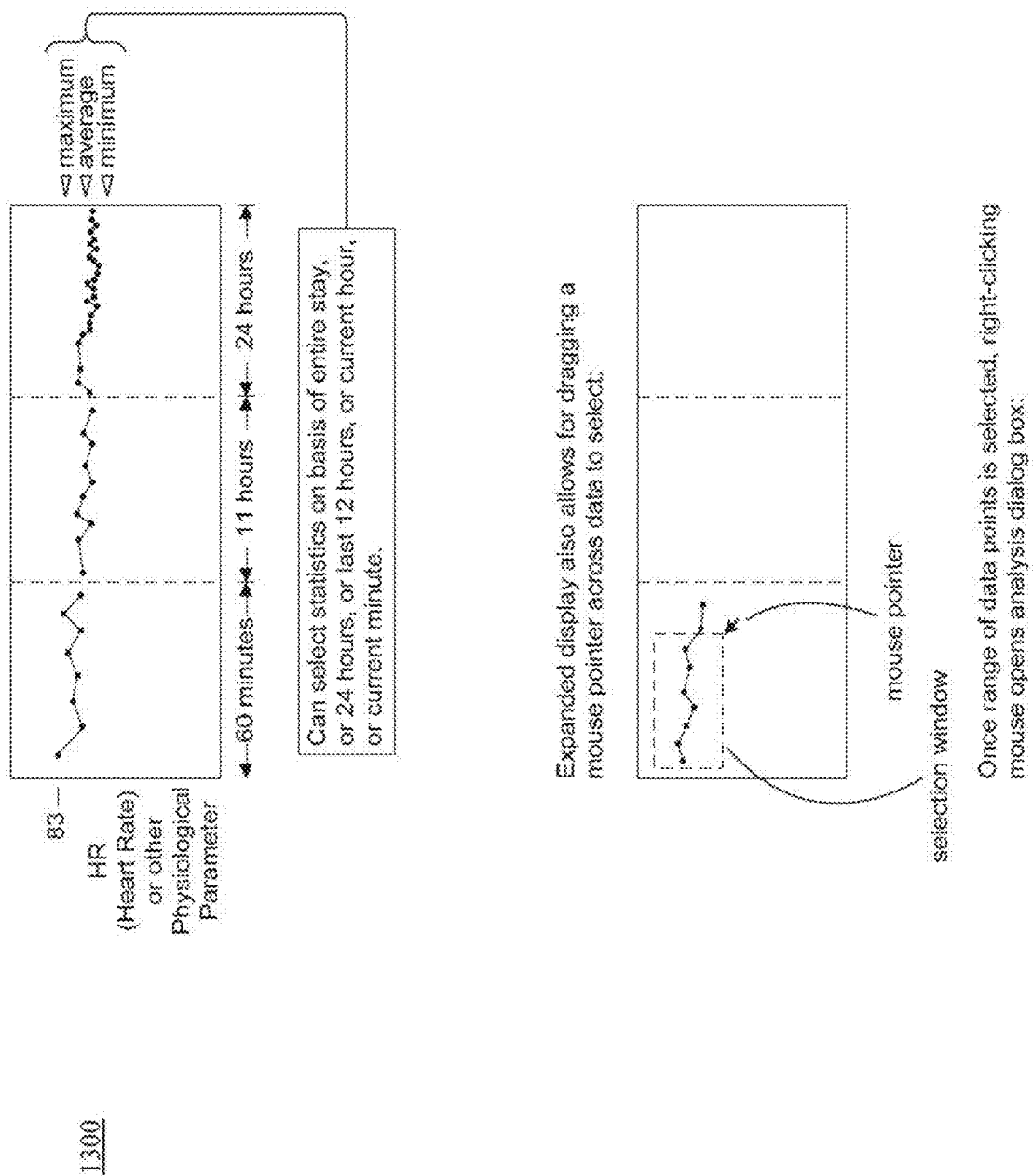
FIG. 13 shows a user-interface with an option to select data.

FIG. 13 shows a user-interface 1300 with an option to select data. In embodiments, the user can drag the mouse over a range of data within the graphical view to select data within that particular range. In embodiments, a dialog box can then be displayed by, e.g., right-clicking a mouse, as described in more detail below.

Figure 14:
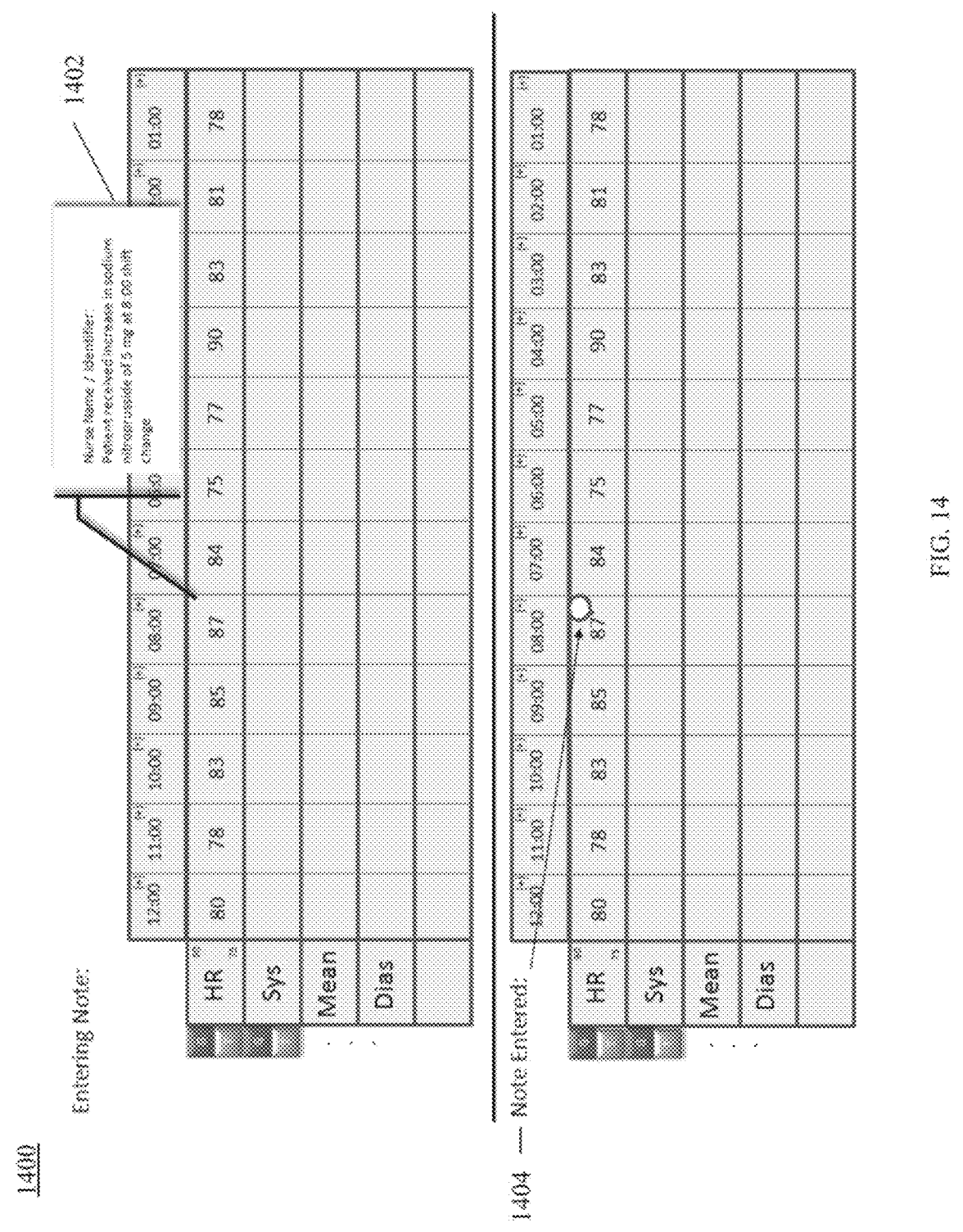

FIG. 14 shows an example of the user-interface 1400 having user comments. In embodiments, a user can provide notes to individualized cells by, e.g., right-clicking within a cell, to open a text dialog 1402. In this way, a clinical user can add relevant contextual information pertinent to a patient at a particular time. For example, each data entry cell can be provided with the capability to enter a 100-character note to accompany the data value. In this way, a clinical user can log event details when a notification is triggered by a threshold and/or rule. In embodiments, an indicator 1404 can be used to notify a user that a note has been entered.

Figure 15:
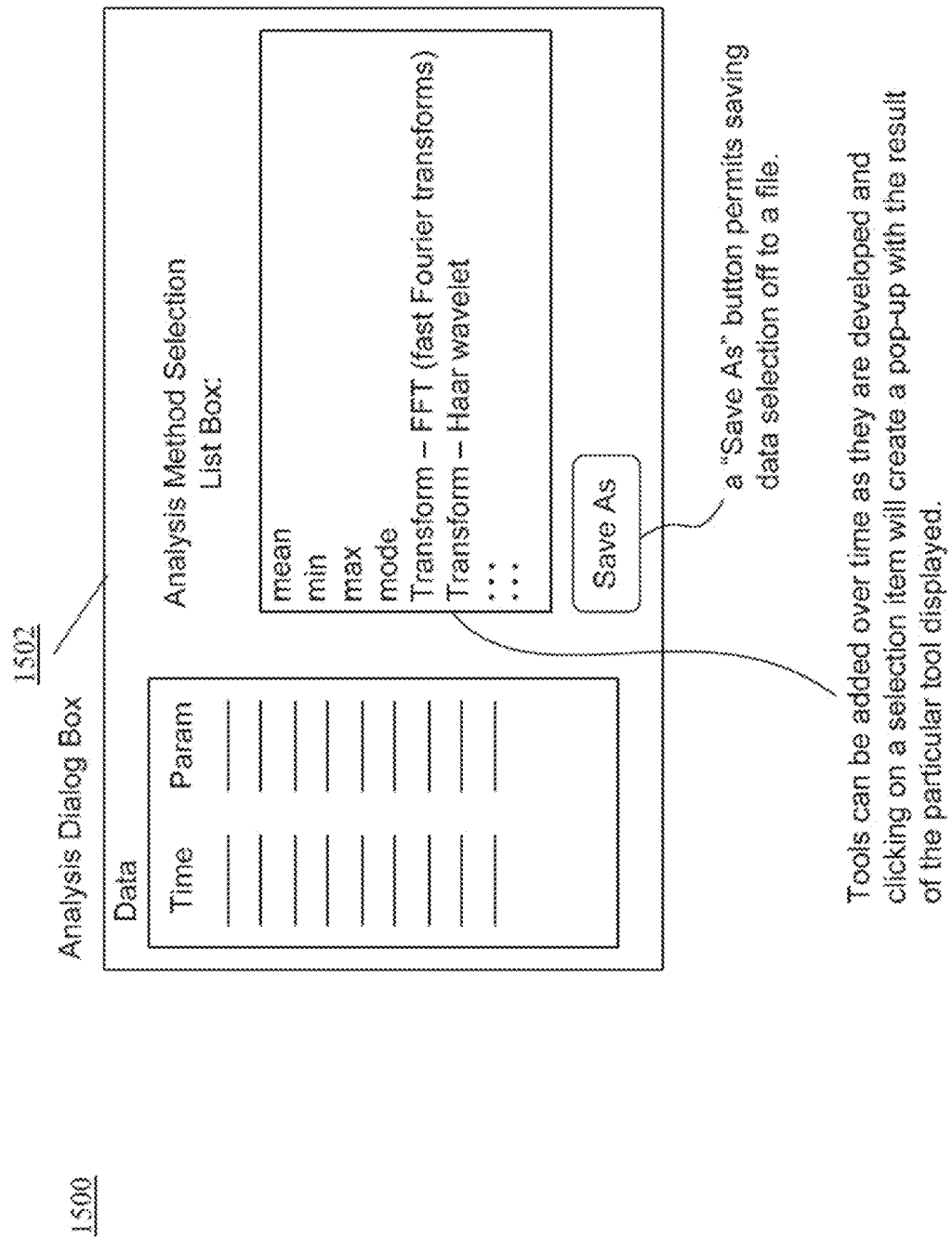
FIG. 15 shows an example of an analysis dialog box.

FIG. 15 shows an example of an analysis dialog box 1500. A set of tools can be displayed enabling a user to apply various thresholds, calculation, and transformative tools to assess, evaluate, project, and analyze the raw data. Examples include simple statistical calculations such as minimums, means, maximums, modes. More complex tools include fast Fourier transforms (FFTs) or wavelet transforms (such as the Haar wavelet). It should be understand that additional tools are further contemplated according to aspects of the present invention.

Figure 16:
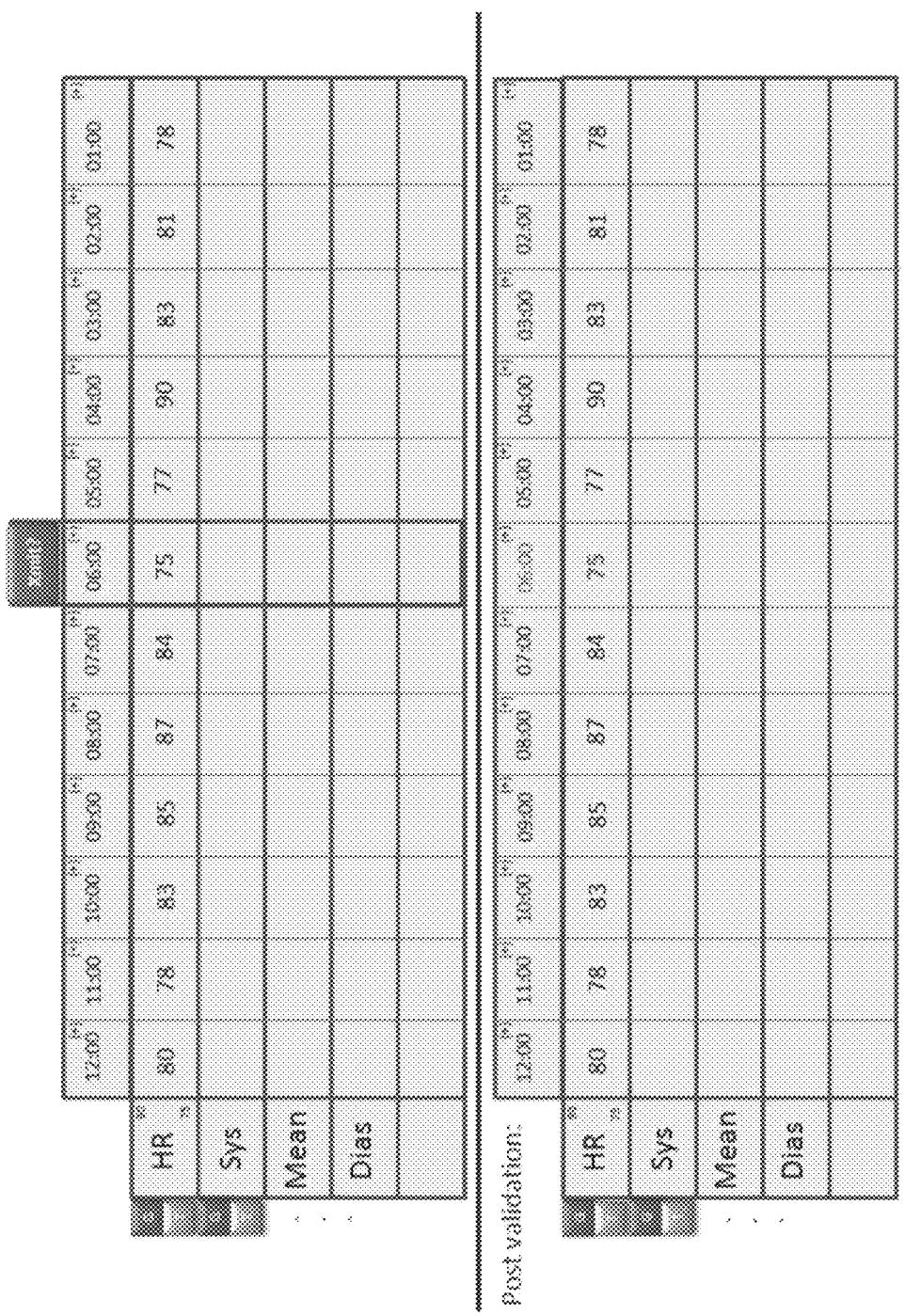
FIG. 16 shows an example user-interface having a transmit button.

FIG. 16 shows an example user-interface 1600 having a transmit button. In embodiments, a user can place a mouse over a top portion of a particular column results, and a validation button "Xmit" can be displayed to the user. The user can click the "Xmit" button to transmit results from the user-interface view to a receiving clinical IT system, such as a departmental information system via HL7.

Figure 17:
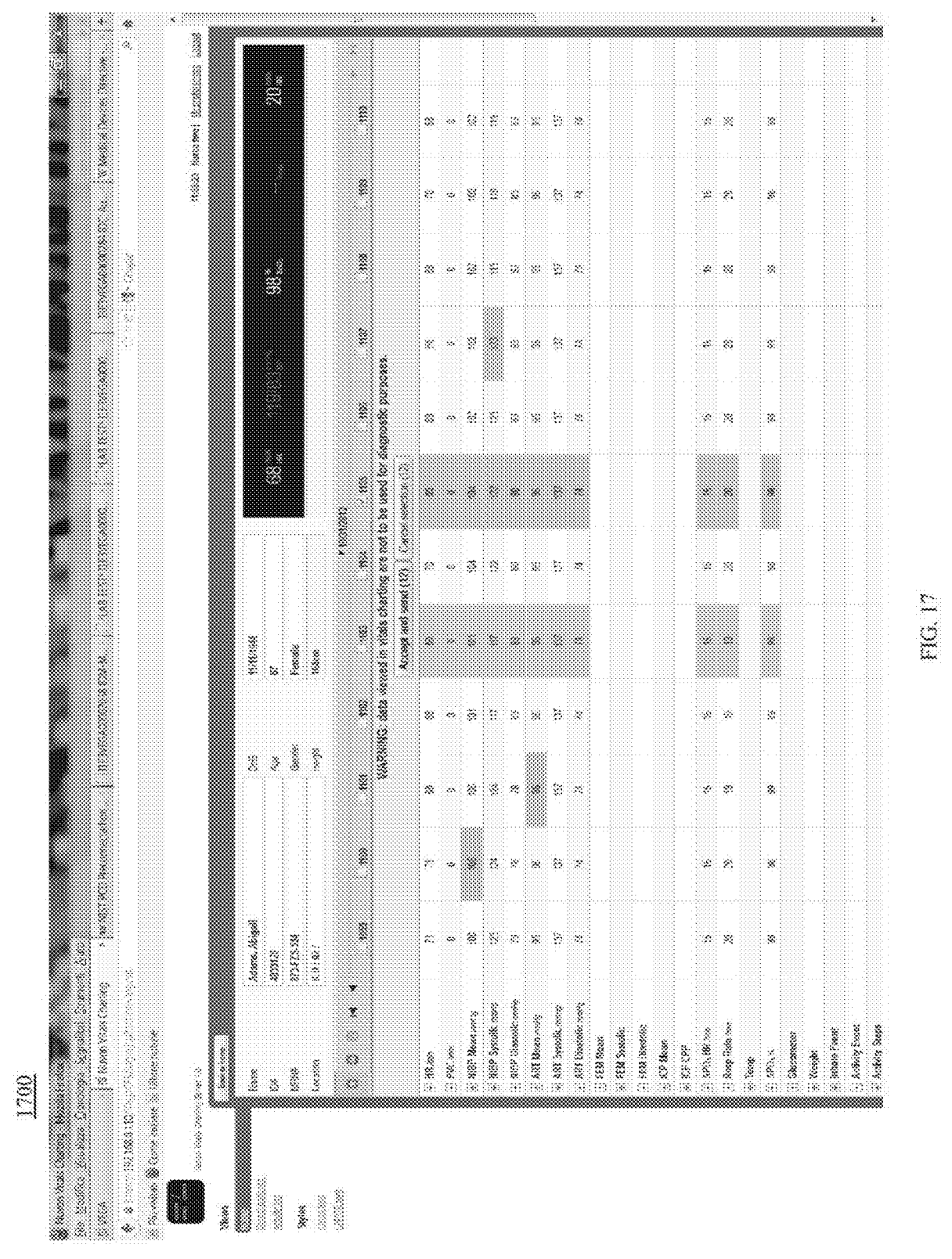

In embodiments, the user can view data and select manually which data to send to the EMR or clinical information system. For example, FIG. 17 illustrates the data selection and validation feature. Data selection can be done singularly or by column, and once data is selected, a confirmation button can be pressed to transmit the selected data to the electronic medical record or clinical information system. In embodiments, a cell/column is shown in a particular color, e.g., green, indicates that data in the cell/column has been sent and received by the EMR or the clinical information system. Alternatively, if data from the selected cell/column has been sent but not yet received by the receiving system, the cell/column can be shown in a second different color, e.g., amber. Yet another option provides that if a cell/column has been selected, but not yet confirmed for transfer, the cell/column can be a third color e.g., lilac. In embodiments, the system can be configured to receive confirmation to transmit the data by clicking an "Accept and Send" button or the "Xmit" button described above. Once confirmed, the cell/column can turn to the second color, and upon receipt of the data from the EMR, the cell/column can turn to the first color. Thus, different colors represent data status of the data. For example, green represents that data sent and available in the EMR or the receiving system, amber represents data sent but not yet received by the receiving system, and lilac represents data selected to be confirmed by clicking the "Accept and Send" button. In this way, data transitions from lilac to amber and then to green.

Figure 18:
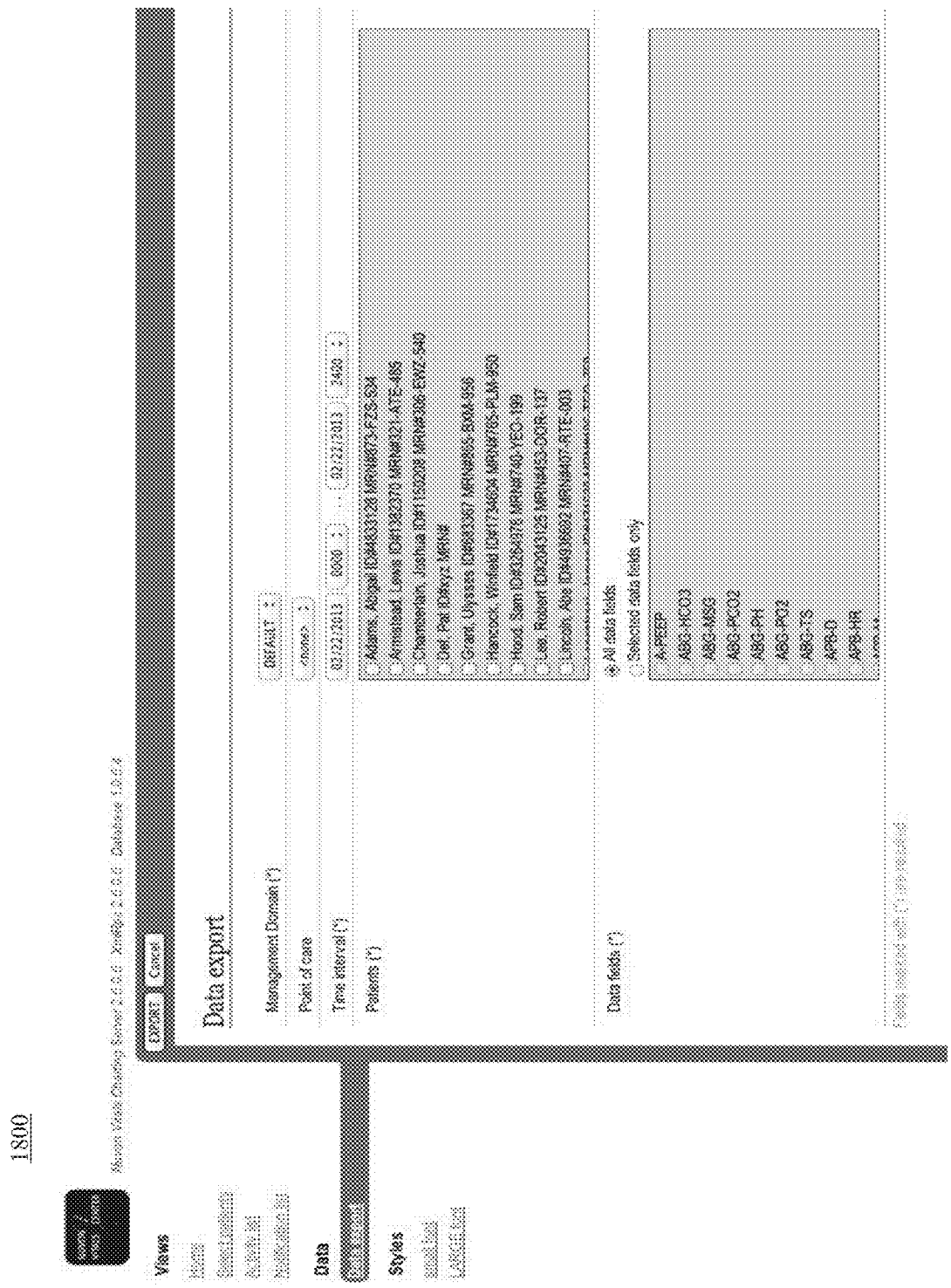
FIG. 18 shows a screenshot of a data export screen.

FIG. 18 shows a screenshot of a data export screen 1800. In embodiments, on the data export form a user can select a desired time interval and patient(s) the export should consider. Users can also select the data fields that the output should contain. Further, the data export screen can be configured to present a subset of patients appearing in the patient selection list. In embodiments, the export format utilizes comma-delimited (CSV). In embodiments, further features include the capability to export resultant rules triggers and threshold triggers via comma-delimited (.CSV) file format along with timestamp of the trigger. Example fields exported to the resulting output file can include: patient ID, time of measurement in "yyyyMMdd HHSSmm" format, data field name, data value and data unit. In embodiments, a first line of the CSV file can be a header for these fields. For example, Table I provides an excerpt from a resulting CSV file taken on a patient simulated every 20 seconds. The time interval of data can be defined by the data collection frequency of the medical device(s) and the medical data collection appliance(s).

TABLE I

| Patient ID, Time, Data field, Value, Unit |
| --- |
| 4833128, 20130222 112110, ETCO2, 32, mmHg |
| 4833128, 20130222 112130, ETCO2, 32, mmHg |
| 4833128, 20130222 112150, ETCO2, 32, mmHg |
| 4833128, 20130222 112210, ETCO2, 33, mmHg |
| 4833128, 20130222 112230, ETCO2, 33, mmHg |
| 4833128, 20130222 112250, ETCO2, 32, mmHg |

10. System Environment(s)

Figure 19:
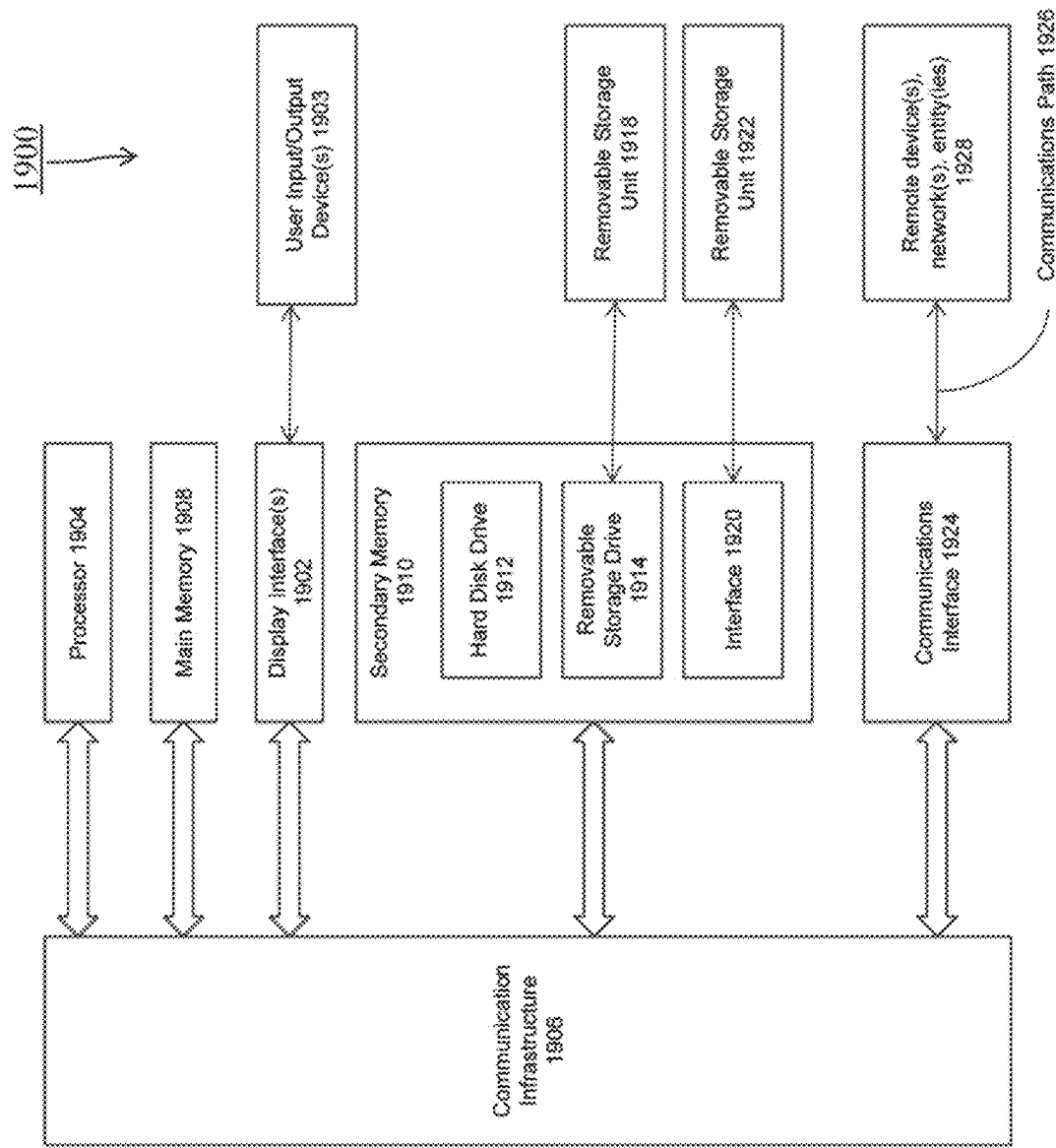
FIG. 19 illustrates a block diagram of a computer system in which embodiments of the present invention, or portions thereof, may be implemented.

Various aspects of the present invention may be implemented in software, firmware, hardware, or a combination thereof. FIG. 19 is an illustration of an example computer system 1900 in which embodiments of the present invention, or portions thereof, can be implemented as computer-readable code. For example, the methods described herein can be implemented in system 1900. Various embodiments of the present invention are described in terms of this example computer system 1900. For example, in embodiments, computer system 1900 can be a client-side device configured to display the user-interfaces 100-1800 described with respect to FIGS. 1-18, respectively. In embodiments, computer system 1900 can be a server-side device configured to collect data and generate notifications based on thresholds and/or user-defined rules as described herein. After reading this description, it will become apparent to a person skilled in the relevant art how to implement embodiments of the present invention using other computer systems and/or computer architectures.

It should be noted that the simulation, synthesis and/or manufacture of various embodiments of this invention may be accomplished, in part, through the use of computer readable code, including general programming languages (such as C or C++), hardware description languages (HDL) such as, for example, Verilog HDL, VHDL, Altera HDL (AHDL), or other available programming and/or schematic capture tools (such as circuit capture tools). This computer readable code can be disposed in any computer-readable medium including a semiconductor, magnetic disk, and/or optical disk (such as CD-ROM, DVD-ROM). As such, the code can be transmitted over communication networks including the Internet. The functions accomplished and/or structure provided by the systems and techniques described above can be represented in a memory.

Computer system 1900 includes one or more processors, such as processor 1904. Processor 1904 is connected to a communication infrastructure 1906 (e.g., a bus or network).

Computer system 1900 also includes a main memory 1908, such as random access memory (RAM), and may also include a secondary memory 1910. Secondary memory 1910 can include, for example, a hard disk drive 1912, a removable storage drive 1914, and/or a memory stick. Removable storage drive 1914 can include a floppy disk drive, a magnetic tape drive, an optical disk drive, a flash memory, or the like. The removable storage drive 1914 reads from and/or writes to a removable storage unit 1918 in a well-known manner. Removable storage unit 1918 can include a floppy disk, magnetic tape, optical disk, flash drive, etc., which is read by and written to by removable storage drive 1914. As will be appreciated by persons skilled in the relevant art, removable storage unit 1918 includes a computer-readable storage medium having stored therein computer software and/or data. Computer system 1900 includes a display interface 1902 (which can include input and output devices 1903 such as keyboards, mice, etc.) that forwards graphics, text, and other data from communication infrastructure 1906 (or from a frame buffer not shown).

In alternative implementations, secondary memory 1910 can include other similar devices for allowing computer programs or other instructions to be loaded into computer system 1900. Such devices can include, for example, a removable storage unit 1922 and an interface 1920. Examples of such devices include a program cartridge and cartridge interface (such as those found in video game devices), a removable memory chip (e.g., EPROM or PROM) and associated socket, and other removable storage units 1922 and interfaces 1920 which allow software and data to be transferred from the removable storage unit 1922 to computer system 1900.

Computer system 1900 can also include a communications interface 1924. Communications interface 1924 allows software and data to be transferred between computer system 1900 and external devices. Communications interface 1924 can include a modem, a network interface (such as an Ethernet card), a communications port, a PCMCIA slot and card, or the like. Software and data transferred via communications interface 1924 are in the form of signals which may be electronic, electromagnetic, optical, or other signals capable of being received by communications interface

1924. These signals are provided to communications interface 1924 via a communications path 1926. Communications path 1926 carries signals and can be implemented using wire or cable, fiber optics, a phone line, a cellular phone link, a RF link or other communications channels.

In this document, the terms "computer program storage medium" and "computer-readable storage medium" are used to generally refer to non-transitory media such as removable storage unit 1918, removable storage unit 1922, and a hard disk installed in hard disk drive 1912. Computer program storage medium and computer-readable storage medium can also refer to memories, such as main memory 1908 and secondary memory 1910, which can be memory semiconductors (e.g., DRAMs, etc.). Embodiments of the present invention can employ any computer-readable medium, known now or in the future. Examples of computer-readable storage mediums include, but are not limited to, non-transitory primary storage devices (e.g., any type of random access memory), and non-transitory secondary storage devices (e.g., hard drives, floppy disks, CD ROMS, ZIP disks, tapes, magnetic storage devices, optical storage devices, MEMS, nanotechnological storage devices, etc.).

These computer program products provide software to computer system 1900. Embodiments of the present invention are also directed to computer program products including software stored on any computer-readable storage medium. Such software, when executed in one or more data processing devices, causes a data processing device(s) to operate as described herein.

Computer programs (also called computer control logic) are stored in main memory 1908 and/or secondary memory 1910. Computer programs may also be received via communications interface 1924. Such computer programs, when executed, enable computer system 1900 to implement embodiments of the present invention as discussed herein. In particular, the computer programs, when executed, enable processor 1904 to implement processes of embodiments of the present invention, such as the steps in the methods described herein can be implemented in system 1900. Where embodiments of the present invention are implemented using software, the software can be stored in a computer program product and loaded into computer system 1900 using removable storage drive 1914, interface 1920, hard drive 1912, or communications interface 1924.

While various embodiments of the present invention have been described above, it should be understood that they have been presented by way of example, and not limitation. It will be apparent to persons skilled in the relevant art(s) that various changes in form and detail can be made therein without departing from the spirit and scope of the invention. Thus, the present invention should not be limited by any of the above described exemplary embodiments, but should be defined only in accordance with the following claims and their equivalents.

Figure 20:
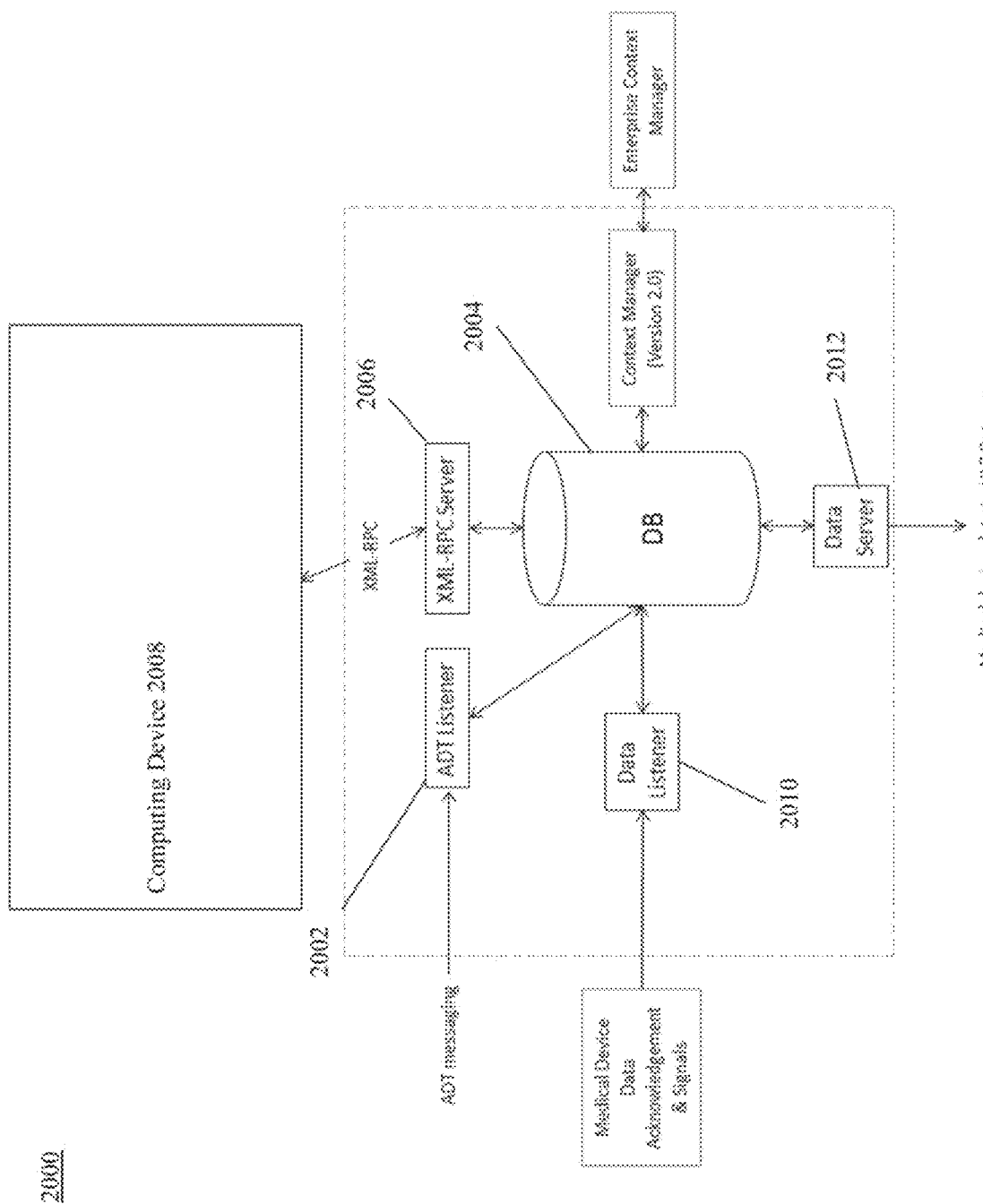
FIG. 20 shows an example system according to aspects of the present invention.

FIG. 20 shows an example system 2000 according to aspects of the present invention. FIG. 20 includes a plurality of internal design modules. In an embodiment, the modules include an ADT Listener 2002 configured to consume patient demographic traffic and populate a database 2004, an XML-RPC Server 2006 (representative of a particular embodiment of the architecture) configured to communicate data to a user-interface on a computing device 2008 and generate notifications sent to a user based on the threshold(s) and/or user defined rules, a data listener 2010 configured to communicate with a system for medical device traffic, and a data server configured to communicate validated data measurements to outbound HL7 Interface Engine, (e.g., an embodiment can include a VEGA System HL7 Interface Engine).

In embodiments, XML-RPC Server 2006 includes a notification tool configured to send a notification tool to the user when a parameter satisfies a user-defined rule and/or exceeds a threshold value. In embodiments, computing device 2008 can be used any computing device, e.g., a smartphone, tablet PC, laptop computers, etc., configured to display user-interfaces 100-1800 described herein. It should be understood by those of ordinary skill in the art that XML-RPC server 2006 and computing device 2008 are only examples and that other types of servers and computing devices are further contemplated according to aspects of the present invention.

In embodiments, multiple types of physiologic monitors or infusion pump systems can communicate through an HL7 gateway, and traffic is differentiated by patient specific identifiers and location. For example, in embodiments, a patient is associated with each bed, and a data collection appliance is associated with each patient. In embodiments, a data collection appliance associated with multiple patients and multiple patients' worth of traffic can be received through a software device driver configured to send different location data, even if they reside on or operate through a data collection appliance. As a result, charting is able to determine location and thus assign data to the correct patient. An additional point of identification for data can be a patient ID.

FIG. 21 shows a system architecture 2100 according to aspects of the present invention. More specifically, FIG. 21 shows a system controller 2102 connected to an HL7 gateway device 2104. The HL7 gateway device 2104 can communicate with a plurality of medical device gates 2106 and a data storage device(s) 2108, such as an EMR, information system(s), or a data warehouse. The HL7 gateway 2104 is further in communication with one or more medical data collection appliances 2110. In turn, the medical data collection appliances 2110 are in communication with a plurality of point of care medical devices 2112. Using the system architecture 2100, users can interact with medical device data collected from bedside medical devices. That is, the system architecture of FIG. 21 can be used to aggregate data which can be displayed using user-interfaces 100-1800.

FIGS. 19-21 illustrate example computer systems in which embodiments of the present invention, or portions thereof, may be implemented as computer-readable code. For example, the user-interfaces 100-1800 may be implemented in one or more computer systems 1900-2100 using hardware, software, firmware, tangible computer-readable media having instructions stored thereon, or a combination thereof and may be implemented in one or more computer systems or other processing systems. In embodiments, user-interfaces 100-1800 may be embodied in hardware, software, or any combination thereof.

In embodiments, the systems described herein can operate using any network or combination of networks that can carry data communications. Such a network may include, but is not limited to, a local area network, metropolitan area network, and/or wide area network such as the Internet. In embodiments, the network can support protocols and technology including, but not limited to, World Wide Web (or simply the "Web"), protocols such as a Hypertext Transfer Protocol ("HTTP") protocols, and/or services. Intermediate web servers, gateways, or other servers may be provided between components of the system shown in FIGS. 19-21, depending upon a particular application or environment.

11. Overview of the Method

FIG. 22 shows a flowchart of an exemplary method 2200, according to an embodiment. At step 2202, the method includes dynamically displaying a parameter associated with a patient. For example, a patient parameter can be shown in a tabular format and toggled to a graphical view as shown in user-interfaces 200-500 of FIGS. 2-5 using, for example, display interface 1902 of FIG. 19. At step 2204, the method further includes receiving at least one of a user-defined rule or a threshold value associated with the parameter. For example, user-defined rules and/or threshold values can be input by a user via user-interfaces 700-1000 shown in FIGS. 7-10 using, for example, display interface 1902 of FIG. 19. At step 2206, the method also includes transmitting, by a computing device, a notification to a user when the at least one of a user-defined rule or the threshold value is triggered. For example, notifications can be sent to the user via user-interfaces 700, 1100 and 1200 of FIGS. 7, 11, and 12, respectively. In embodiments, notifications can be sent to a user via an email, pager, HL7 notification, etc. instead of, or in addition to, being displayed on a user-interface.

The embodiments described herein are provided for illustrative purposes, and are not limiting. Other embodiments are possible, and modifications can be made to the embodiments within the spirit and scope of the present invention. Therefore, the Detailed Description is not meant to limit the present invention. Rather, the scope of the present invention is defined only in accordance with the following claims and their equivalents.

Some embodiments of the invention may be implemented in hardware, firmware, software, or any combination thereof. Some embodiments of the invention can also be implemented as instructions stored on a machine-readable medium, which can be read and executed by one or more processors. A machine-readable medium can include any mechanism for storing or transmitting information in a form readable by a machine (e.g., a computing device). For example, a machine-readable medium can include non-transitory machine-readable mediums such as read only memory (ROM); random access memory (RAM); magnetic disk storage media; optical storage media; flash memory devices; and others. As another example, the machine-readable medium can include transitory machine-readable medium such as electrical, optical, acoustical, or other forms of propagated signals (e.g., carrier waves, infrared signals, digital signals, etc.). Further, firmware, software, routines, instructions can be described herein as performing certain actions. However, it should be appreciated that such descriptions are merely for convenience and that such actions in fact result from computing devices, processors, controllers, or other devices executing the firmware, software, routines, instructions, etc.

It is to be understood that the phraseology or terminology herein is for the purpose of description and not of limitation, such that the terminology or phraseology of the present specification is to be interpreted by those skilled in relevant art(s) in light of the teachings herein.

What is claimed:

1. A system operating on real-time data derived from a plurality of data sources for supporting user-definable rules and providing user notifications comprising a computing device configured to:
generate a user-interface configured to dynamically display one or more parameters and toggle between a tabular display and a graphical display;
receive at least one of a user-defined rule or a threshold value associated with the parameter from a user-interface element, wherein the user-defined rule or the threshold value are definable using a scripting language; and
provide a notification to a user when the one or more parameters satisfies the user-defined rule or exceeds the threshold value, wherein the user-defined rule comprises mathematical relations and conditional expressions,
wherein access to create or modify the user-defined rules and threshold values is limited based on different classes of users such as clinical users, non-clinical users, or other classes of user.

2. The system of claim 1, wherein the threshold value comprises a plurality of proximal threshold levels corresponding to respective levels of notification, the proximal threshold values comprising:
a first threshold value having a first level of notification; and
a second threshold value having a second level of notification, the second level of notification indicating a higher level of severity of the parameter associated with the threshold values.

3. The system of claim 1, wherein the notification includes a visual icon indicating a relative value of the parameter which triggered the notification.

4. The system of claim 1, wherein the notification is based on the user-defined rule and the threshold value.

5. The system of claim 1, wherein the user-defined rule or the threshold value is tailored to a specific patient or a specific department.

6. The system of claim 1, wherein:
the user-defined rule includes a plurality of user-defined rules and the threshold value includes a plurality of threshold values, each of the user-defined rules and the threshold values having an assigned numeric value; and
the computing device is further configured to compare the numeric values of the user-defined rules and threshold values to determine which notification is sent to the user.

7. A method providing user notifications and smart alarms, comprising:
dynamically displaying a parameter associated with a patient;
receiving at least one of a user-defined rule or a threshold value associated with the parameter, wherein the user-defined rule or the threshold value are definable using a scripting language; and
prioritizing triggering of at least one of the user-defined rule or the threshold value based on numerical values assigned to the user-defined rule or threshold value, respectively;
transmitting, by a computing device, a notification to a user when the at least one of a user-defined rule or the threshold value is triggered,
wherein access to create or modify the user-defined rules and threshold values is limited based on different classes of users such as clinical users, non-clinical users, or other classes of user.

8. The method of claim 7, further comprising receiving user comments via a user-interface element when the user is sent the notification.

9. The method of claim 7, wherein the notification comprises a plurality of notifications based on one or more user-defined rules and/or threshold values, the plurality of notifications being color coded to indicate varying levels of alerts.

10. The method of claim 7, wherein the user-defined rule is written using a scripting language, and includes mathematical relations and conditional expressions.

11. The method of claim 7, wherein at least one of the user-defined rule or the threshold value is tailored to a specific patient or a specific department.

12. The method of claim 7, wherein the user-defined rule describes at least one of a user or a group of users to receive the notification.

13. A non-transitory computer-readable medium storing software comprising instructions executable by one or more computers which, upon execution, cause the one or more computers to perform operations comprising:
generating a user-interface configured to dynamically display a parameter and toggle between a tabular display and a graphical display;
receiving, via a computing device, at least one of a user-defined rule or a threshold value associated with a parameter associated with a patient, wherein the user-defined rule or the threshold value are definable using a scripting language; and
processing a notification when the at least one of the user-defined rule or the threshold value is triggered, wherein access to create or modify rules and threshold values is limited based on different classes of users such as clinical users, non-clinical users, or other classes of user, wherein the user-defined rule comprises mathematical relations and conditional expressions.

14. The non-transitory computer readable storage medium of claim 13, wherein the instructions cause the processor to further perform:
generating alerts based on the threshold value having a specified color associated with the threshold value, wherein:
a patient having acceptable readings is displayed having a first color;
a patient having an low-level alert is displayed having a second color;
a patient having a high-level alert is displayed having a third color; and
a patient having a customizable level of alert having a user-defined color.

15. The non-transitory computer readable storage medium of claim 14, wherein the notification transmitted to the user is color coded based on a color corresponding to the displayed alerts.

16. The non-transitory computer readable storage medium of claim 13, wherein the instructions cause the processor to further perform:
modifying an existing user-defined rule or threshold value.

17. The non-transitory computer readable storage medium of claim 13, wherein the instructions cause the processor to further perform:
receiving user comments via a text box when the user is sent the notification.

18. A system for supporting user-definable rules and providing user notifications to a user by operating on real time data derived from a plurality of medical devices, the system comprising:
a server computer configured to:
receive data from the plurality of heterogeneous medical devices;
dynamically generate a user-interface in response to receiving real time data from the plurality of heterogeneous medical devices and configured to dynamically display the real time data;
receive at least one user-defined rule or parameter threshold, the at least one user-defined rule or parameter threshold being associated with at least one of the plurality of heterogeneous medical devices sources, wherein the at least one user-defined rule or the parameter threshold are definable using a scripting language;
prioritize triggering of at least one of the user-defined rule or the threshold value based on numerical values assigned to the user-defined rule or threshold value, respectively;
provide a notification to the user in response to the at least one user-defined rule or threshold and the real time data from the plurality of heterogeneous medical devices, wherein access to create or modify the at least one user-defined rule and parameter threshold is limited based on different classes of users such as clinical users, non-clinical users, or other classes of user; and
a client computer in communication with the server computer, the client computer displaying to the user the generated user-interface and the notifications.

* * * * *